(12) United States Patent
Kasper et al.

(10) Patent No.: US 8,030,458 B2
(45) Date of Patent: Oct. 4, 2011

(54) MONOCLONAL ANTIBODIES TO TACROLIMUS AND IMMUNOASSAYS METHODS FOR TACROLIMUS

(75) Inventors: Kenneth Cornell Kasper, Monte Sereno, CA (US); Henry Jeong, Palo Alto, CA (US); Dariush Davalian, San Jose, CA (US); Hshiou-ting Liu, Milpitas, CA (US); Paul Levi Miller, South San Francisco, CA (US); Denise Leah Williams, San Jose, CA (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 314 days.

(21) Appl. No.: 12/239,063

(22) Filed: Sep. 26, 2008

(65) Prior Publication Data

US 2009/0087865 A1   Apr. 2, 2009

Related U.S. Application Data

(62) Division of application No. 11/441,644, filed on May 26, 2006, now abandoned, which is a division of application No. 09/368,010, filed on Aug. 3, 1999, now Pat. No. 7,078,495.

(51) Int. Cl.
*C07K 16/00* (2006.01)
*G01N 33/53* (2006.01)
*G01N 21/76* (2006.01)

(52) U.S. Cl. ............... 530/388.9; 530/389.8; 530/391.3; 435/7.1; 436/172; 436/815

(58) Field of Classification Search .................. None
See application file for complete search history.

(56) References Cited

U.S. PATENT DOCUMENTS

| 3,817,837 A | 6/1974 | Rubinstein et al. |
| 5,532,137 A | 7/1996 | Niwa et al. |
| 5,635,406 A | 6/1997 | Grenier et al. |

FOREIGN PATENT DOCUMENTS

| EP | 0293892 | 12/1988 |
| JP | 01-92659 A | 4/1989 |
| JP | 01-131200 | 5/1989 |
| WO | 94/04700 | 3/1994 |
| WO | 94/25022 | 11/1994 |
| WO | 94/25022 A | 11/1994 |
| WO | 96/02004 A | 1/1996 |
| WO | 96/41184 A | 12/1996 |

OTHER PUBLICATIONS

M. Oellerich. Enzyme-immunoassay: a review. J. CLin. Chem. Clin. Biochem 1984, vol. 22, No. 12, pp. 895-904.*
Iwasaki et al. Further metabolism of FK506( Tacrolimus). Identification and biological activities of the metabolites oxidized at multiple sites of FK506. Drug Metabolism and Disposition 1995, vol. 23, No. 1, pp. 28-34.*
G. Wiederrecht et al, "The Mechanism of Action of FK-506 and Cyclosporin A" Ann. N.Y. Acad. Sci. 696,9-19 (1993).
M.L. Cleary & J. Sklar, "Lymphoproliferative Disorders in Cardiac Transplant Recipients are Multiclonal Lymphomas", Lancet 2, 49-493 (1984).
L.J. Swinnen et al, "Increased Incidence of Lymphoproliferative Disorder after Immunosuppression with a Monoclonal Antibody OKT3 . . . " New England Journal of Medicine 323, 1723-1728 (1990).
B.Z. Katz et al.,"Latent and Replicating Forms of Epstein-Barr Virus DNA and Lymphomas in Lymphoprliferative Diseases" Journal of Infect. Dis., 160, 589-598 (1989).
J.S. Huston et al., "Protein Engineering of Antibody Binding Sites: Recovery of Specific Activity in an Anti-Digoxin . . . " Proc. Nat. Acad. Science, USA 85, 5879-5883 (1988).
G.T. Hermanson, "Bioconjugate Techniques" Academic Press, San Diego, 570-592, 1996.
P.J. Taylor et al., "Sensitive, Specific Quantative Analysis of Tacrolimus (FK506) in Blood by Liquid Chromatography-Electrospray Tandem . . . " Clin. Chem. 42, 279-285 (1996).
H.J. Jeong et al., "New Monoclonal Antibody for the Immunosuppressive Drug Tacrolimus", Ther. Drug Monit. 21, 444 (Aug. 1999), Abstract No. 65.
V.W. Armstrong et al., "Evaluation of an EMIT Tacrolimus Assay: Comparison with Pentamer Formation Assay and . . . ", Ther. Drug Monit. 21, 448(Aug. 1999), Abstract No. 80.
L. Backman et al. "Transplantation" 57(4), 519-525 (1994).
Alak, Ala M., "Measurement of Tacrolimus (FK506) and Its Metabolites: A Review of Assay Development and Application in Therapeutic Drug Monitoring and Pharmacokenetic Studies," Therapeutic Drug Monitoring, vol. 19, pp. 338-351, 1997, Lippincot-Raven Pub., Philadelphia.
Murthy et al., "Tacrolimus Metabolite Cross-Reactivity in Different Tacrolimus Assays," Clinical Biochemistry, vol. 31, No. 8, pp. 613-617, 1998.

* cited by examiner

*Primary Examiner* — Shafiqul Haq
(74) *Attorney, Agent, or Firm* — Theodore J. Leitereg

(57) ABSTRACT

An IgG$_1\lambda$ monoclonal antibody to the immunosuppressive drug tacrolimus has improved properties. In particular, this monoclonal antibody, designated 1H6, has reduced cross-reactivity to several tacrolimus metabolites. This antibody is suitable for performance of immunoassays such as homogeneous immunoassays to detect or determine the presence or concentration of tacrolimus in samples such as blood samples. The invention further includes derivatives of tacrolimus derivatized at a non-binding portion of the molecule useful in immunizing antibody-producing animals and in producing such monoclonal antibodies, as well as labeled derivatives of tacrolimus useful as tacrolimus analogues in such assays. The invention further includes immunoassay methods for the detection of tacrolimus and test kits useful in performing such immunoassays.

16 Claims, 13 Drawing Sheets

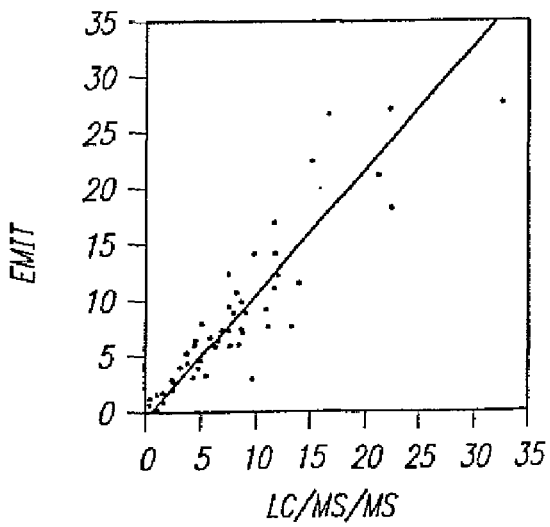
FIG. 12
FIG. 13
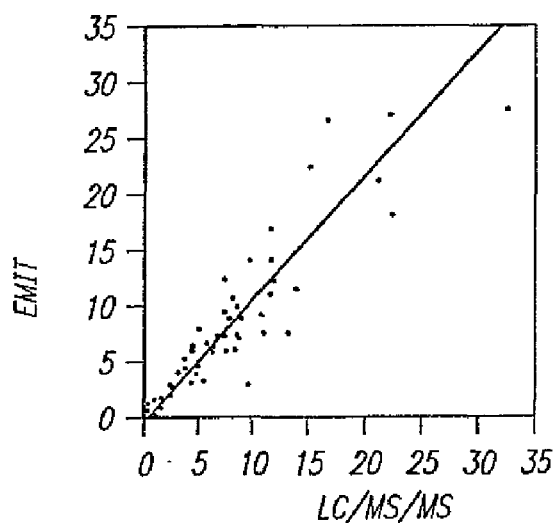
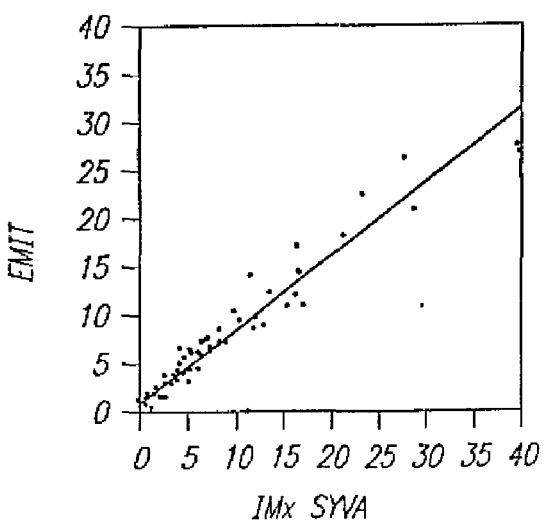
FIG. 14

US 8,030,458 B2

MONOCLONAL ANTIBODIES TO TACROLIMUS AND IMMUNOASSAYS METHODS FOR TACROLIMUS

This application is a divisional of U.S. Ser. No. 11/441,644, filed May 26, 2006, now pending, which is a divisional of U.S. Ser. No. 09/368,010, filed Aug. 3, 1999, which is now U.S. Pat. No. 7,078,495.

FIELD OF THE INVENTION

This invention is directed to monoclonal antibodies to tacrolimus, methods for producing such monoclonal antibodies, and derivatives of tacrolimus useful for producing such monoclonal antibodies.

BACKGROUND OF THE INVENTION

Tacrolimus is a macrolide isolated from *Streptomyces tsukubaensis*. Tacrolimus has the chemical name [3S-[3R*[E(1S*,3S*,4S*)],4S*,5R*,8S*,9E,12R*,14R*,15S*,16R*,18S*,19S*,26aR*]]-5,6,8,11,12,13,14,15,16,17,18,19,24,25,26,26a-hexadecahydro-5,19-dihydroxy-3-[2-(4-hydroxy-3-methoxycylohexyl)-1-methylethenyl]-14,16-dimethoxy-4,10,12,18-tetramethyl-8-(2-propenyl)-15,19-epoxy-3H-pyrido[2,1-c][1,4]-oxaazacyclotricosine-1,7,20,21(4H,23H) tetrone. The structure of tacrolimus, giving the numbering, is shown below in FIG. 16.

Tacrolimus is also known as FR-900506 or FK-506. Tacrolimus has immunosuppressive activity and antimicrobial activity.

The immunosuppressive activity of tacrolimus is particularly important and has led to the increasingly wide use of this drug. Immunosuppression is used clinically in a number of contexts, most importantly in preventing rejection in organ transplantation. Immunosuppressive drugs are also administered in prevention of Rh hemolytic disease of the newborn and in the treatment of autoimmune disorders. Tacrolimus inhibits T-cell activation by binding to a cytosolic protein known as FKBP (FK506 binding protein). The drug-binding protein complex stably associates with calcineurin. This inhibits the serine-threonine phosphatase activity of this $Ca^{2+}$-dependent enzyme. This inhibits calcineurin-dependent activation of lymphokine expression, apoptosis, and degranulation (G. Wiederrecht et al., "The Mechanism of Action of FK-506 and Cyclosporin A," *Ann. N.Y. Acad. Sci.* 696:9-19 (1993)).

Tacrolimus can be administered intravenously in a short or continuous infusion or orally. Tacrolimus, like other immunosuppressant agents, has a spectrum of toxicity. The major toxicity associated with clinical use of the drug is nephrotoxicity. In addition, neurotoxicity can develop, associated with headache, tremor, insomnia, pain, or other symptoms. Additionally, gastrointestinal toxicity manifested by diarrhea or nausea can develop, as can cardiovascular toxicity manifested by hypertension.

Additionally, metabolic toxicity can develop as manifested by the development of such symptoms as hyperkalemia, hypomagnesemia, or hyperglycemia. In addition, long-term immunosuppression with tacrolimus can produce increased risk of all types of infections, not only the usual bacterial, viral, and fungal pathogens, but also various unusual opportunistic infections as well.

Additionally, there is an increased risk of lymphomas and related malignancies associated with the administration of tacrolimus (M. L. Cleary & J. Sklar, "Lymphoproliferative Disorders in Cardiac Transplant Recipients are Multiclonal Lymphomas," *Lancet* 2:49-493 (1984); L. J. Swinnen et al., "Increased Incidence of Lymphoproliferative Disorder After Immunosuppression with a Monoclonal Antibody OKT3 in Cardiac-Transplant Recipients," *N. Engl. J. Med.* 323:1723-1728 (1990)). At least some of these malignancies are related to impaired immune responses to Epstein-Barr virus (B. Z. Katz et al., "Latent and Replicating Forms of Epstein-Bair virus DNA and Lymphomas in Lymphoproliferative Diseases," *J. Infect. Dis.*, 160:589-598 (1989)).

The potency and the spectrum of toxicities of tacrolimus requires sensitive, reproducible, and reliable methods for monitoring the blood concentration of these compounds after administration to a patient, such a patient undergoing organ transplantation. It is important that such methods be sensitive enough to detect low concentrations of tacrolimus. It is also important that such methods be reliable and reproducible, and avoid interference from compounds such as metabolites of tacrolimus.

Although antibodies and immunoassays to tacrolimus exist, and are described, for example, in U.S. Pat. No. 5,532,137 to Niwa et al., incorporated herein by this reference, there is still a need for the development of improved antibodies and immunoassays specific for tacrolimus. There is, particularly, a need for improved monoclonal antibodies to tacrolimus that can be used in developing a sensitive, reliable, and reproducible immunoassay for tacrolimus.

The development of a reliable immunoassay for tacrolimus is complicated by the fact that tacrolimus has a number of metabolites that are found in the blood of an individual being treated with tacrolimus. The conversion of tacrolimus to these metabolites involve demethylation, hydroxylation, and ring formation. It is important that antibodies to tacrolimus have as little cross-reactivity with these derivatives as possible.

There is therefore a need for the development of improved monoclonal antibodies to tacrolimus that are useful for immunoassays for tacrolimus and that possess a minimal degree of cross-reactivity to tacrolimus metabolites. There is also a need for improved immunoassays using such monoclonal antibodies for the detection and determination of tacrolimus in the blood of patients being administered tacrolimus.

SUMMARY

We have discovered that tacrolimus, when derivatized in the non-binding domain, can be coupled to a high molecular weight carrier such as a protein for immunization to produce antibodies. The resulting antibody-producing cells can be used to generate monoclonal antibodies by cell fusion. These monoclonal antibodies have desirable properties, including reduced cross-reactivity with tacrolimus metabolites.

One embodiment of the present invention is a monoclonal antibody to tacrolimus that is a monoclonal antibody designated 1H6 and which has less than about 8% cross-reactivity with each of 15-demethyl tacrolimus, 31-demethyl tacrolimus, 13,31-didemethyl tacrolimus, 15,31-didemethyl tacrolimus and 12-hydroxy tacrolimus.

Another embodiment of the present invention is a monoclonal antibody to tacrolimus that:

(1) competes with the $IgG_1\lambda$ monoclonal antibody designated 1H6 at least about 80% as effectively on a molar basis as compared with the $IgG_1\lambda$ monoclonal antibody designated 1H6 as measured by competition assays; and (2) has less than about 10% cross-reactivity with each of 15-demethyl tacrolimus, 31-demethyl tacrolimus, 13,31-didemethyl tacrolimus, 15,31-didemethyl tacrolimus, and 12-hydroxy tacrolimus. Preferably, the monoclonal antibody to tacrolimus competes at least about 90% as effectively on a molar basis as the monoclonal antibody designated 1H6 and has less than about 8% cross-reactivity with each of 15-demethyl tacrolimus, 31-demethyl tacrolimus, 13,31-didemethyl tacrolimus, 15,31-didemethyl tacrolimus and 12-hydroxy tacrolimus.

Another embodiment of the present invention is a hybridoma producing the $IgG_1\lambda$ monoclonal antibody to tacrolimus designated 1H6 as described above.

Yet another embodiment of the present invention is a hybridoma producing a monoclonal antibody that:

(1) competes with the $IgG_1\lambda$ monoclonal antibody designated 1H6 at least about 80% as effectively on a molar basis as compared with the $IgG_1\lambda$ monoclonal antibody designated 1H6 as measured by competition assays; and (2) has less than about 10% cross-reactivity with each of 15-demethyl tacrolimus, 31-demethyl tacrolimus, 13,31-didemethyl tacrolimus, 15,31-didemethyl tacrolimus, and 12-hydroxy tacrolimus.

Another embodiment of the present invention is a monoclonal antibody that:

(1) competes with the $IgG_1\lambda$ monoclonal antibody designated 1H6 at least about 80% as effectively on a molar basis as compared with the $IgG_1\lambda$ monoclonal antibody designated 1H6 as measured by competition assays; and (2) has less than about 10% cross-reactivity with each of 15-demethyl tacrolimus, 31-demethyl tacrolimus, 13,31-didemethyl tacrolimus, 15,31-didemethyl tacrolimus, and 12-hydroxy tacrolimus, wherein at least some of the constant regions of the antibody are replaced by human constant regions so that the monoclonal antibody is humanized.

Yet another embodiment of the present invention is a single-chain recombinant antibody (sFv) including therein the variable regions of an antibody to tacrolimus that:

(1) competes with the $IgG_1\lambda$ monoclonal antibody designated 1H6 at least about 80% as effectively on a molar basis as compared with the $IgG_1\lambda$ monoclonal antibody designated 1H6 as measured by competition assays; and (2) has less than about 10% cross-reactivity with each of 15-demethyl tacrolimus, 31-demethyl tacrolimus, 13,31-didemethyl tacrolimus, 15,31-didemethyl tacrolimus, and 12-hydroxy tacrolimus.

Still another embodiment of the present invention is a monoclonal antibody to tacrolimus produced by fusion of antibody-producing cells from an antibody-producing mammal immunized with tacrolimus derivatized with a carboxymethyl oxime moiety at a carbon atom in the non-binding domain of tacrolimus conjugated to a high molecular weight protein with a suitable fusion partner. Preferably, the carbon atom in the non-binding domain of tacrolimus is carbon 22. Preferably, the high molecular weight protein is keyhole limpet hemocyanin.

Yet another embodiment of the present invention is a monoclonal antibody to tacrolimus that is an $IgG_1\lambda$ monoclonal antibody, that has a binding affinity for tacrolimus of about $3.7 \times 10^9$ liters/mole, that cross-reacts with 13-demethyl tacrolimus, and that has less than about 8% cross-reactivity to all of the following tacrolimus metabolites: 15-demethyl tacrolimus; 31-demethyl tacrolimus; 13,31-didemethyl tacrolimus; 15,31-didemethyl tacrolimus; and 12-hydroxy tacrolimus.

Another aspect of the present invention is antibodies, including polyclonal antibodies, produced by immunization of an antibody-producing mammal with tacrolimus derivatized with a carboxymethyl oxime moiety at a carbon atom in the non-binding domain of tacrolimus conjugated to a high molecular weight protein. Preferably, the carbon atom in the non-binding domain of tacrolimus is carbon 22. Preferably, the high molecular weight protein is keyhole limpet hemocyanin.

Another aspect of the present invention is a conjugate comprising an antibody according to the present invention directly or indirectly conjugated to a detectable label. The detectable label can be selected from the group consisting of an enzyme label, a radioactive label, a fluorescent label, a chemiluminescent label, a bioluminescent label, and a particulate label. In many applications, the label is preferably an enzyme label.

Still another aspect of the present invention is a method of detecting or determining tacrolimus comprising the steps of:

(1) providing a sample suspected of containing tacrolimus;

(2) reacting the sample with:

(a) an antibody according to the present invention; and (b) optionally, a tacrolimus analogue; wherein one of the antibody or the tacrolimus analogue is labeled with a label producing a detectable signal; and (3) observing or measuring one of:

(a) the signal associated with tacrolimus bound to antibody;

(b) the signal associated with tacrolimus unbound to antibody; or (c) the total signal present;

in order to detect or determine the presence or concentration of tacrolimus in the sample.

Typically, in this method, the sample is reacted with a tacrolimus analogue labeled with an enzyme-label and the total signal present is observed or measured to detect or determine the presence or concentration of tacrolimus in the sample.

Another aspect of the present invention is a test kit comprising, packaged in separate containers:

(1) an antibody according to the present invention; and (2) a tacrolimus analogue labeled directly or indirectly with an enzyme label.

Yet another aspect of the present invention is a derivative of tacrolimus comprising tacrolimus that is derivatized with a carboxymethyl oxime moiety at a carbon atom in the non-binding domain of tacrolimus. Preferably, the carbon atom in the non-binding domain of tacrolimus is carbon 22.

Still another aspect of the present invention is a conjugate comprising a derivative of tacrolimus as described above conjugated to a high molecular weight protein. Preferably, the high molecular weight protein is keyhole limpet hemocyanin.

Yet another aspect of the present invention is a method of derivatizing tacrolimus comprising reacting tacrolimus with carboxymethoxylamine to produce a carboxymethyl oxime derivative of tacrolimus, the carboxymethyl oxime moiety being located at carbon atom 22.

Still another aspect of the present invention is a method of producing a conjugate of tacrolimus with a high molecular weight protein comprising:

(1) reacting tacrolimus with carboxymethoxylamine to produce a carboxymethyl oxime derivative of tacrolimus, the carboxymethyl oxime moiety being located at carbon atom 22;

(2) activating the carboxymethyl oxime to produce a reactive N-hydroxysuccinimide ester; and (3) reacting the N-hydroxysuccinimide ester with the high molecular weight protein to produce the conjugate.

Another aspect of the present invention is a derivative of tacrolimus comprising tacrolimus substituted with a carboxymethyl oxime moiety at carbon atom 22 linked through a linker to a biotin moiety. In one preferred embodiment of this aspect of the present invention, the linker has the structure NH$_2$—CH$_2$—CH$_2$—NH—CO—(CH$_2$)$_5$—NH$_2$, and one amine group of the linker forms an amide bond with the carboxyl group of the carboxymethyl oxime and the other amine group of the linker forms an amide bond with the carboxyl group of the biotin.

Still another aspect of the present invention is a method of derivatizing tacrolimus comprising:

(1) reacting tacrolimus with carboxymethoxylamine to produce a carboxymethyl oxime derivative of tacrolimus, the carboxymethyl oxime derivative being located at position 22;

(2) activating the carboxymethyl oxime to produce a reactive N-hydroxysuccinimide ester; and (3) reacting the N-hydroxysuccinimide ester with the carboxyl group of biotin or a biotin derivative or analogue.

Yet another aspect of the present invention is a derivative of tacrolimus comprising tacrolimus that is derivatized with a bromoacetyl moiety at a carbon atom in the non-binding domain of tacrolimus. Preferably, the carbon atom in the non-binding domain is carbon atom 22. These derivatives can then be reacted with an enzyme or other protein to produce a conjugate containing the derivative conjugated to a protein, such as an enzyme. In one preferred embodiment, the protein is a cysteine-containing mutein of glucose-6-phosphate dehydrogenase.

Accordingly, another aspect of the present invention is a method of derivatizing tacrolimus comprising:

(1) reacting tacrolimus with carboxymethoxylamine to produce a carboxymethyl oxime derivative of tacrolimus, the carboxymethyl oxime derivative being located at position 22;

(2) activating the carboxymethyl oxime to produce a reactive N-hydroxysuccinimide ester; and (3) reacting the N-hydroxysuccinimide ester with the trifluoroacetic acid salt of bromoacetyl ethylenediamine to produce a bromoacetyl derivative of tacrolimus.

BRIEF DESCRIPTION OF THE DRAWINGS

These and other features, aspects, and advantages of the present invention will become better understood with reference to the following description, appended claims, and accompanying drawings where:

FIG. 12 is a graph showing the correlation between the results for the assay of tacrolimus using a homogeneous enzyme immunoassay with the monoclonal antibody for which the calibration curve is shown in FIG. 11 and the results for the assay of tacrolimus using a method employing gas chromatography and tandem mass spectroscopy (LC/MS/MS);

FIG. 13 is a graph showing the correlation between the results for the assay of tacrolimus using the homogeneous enzyme immunoassay and using LC/MS/MS on a panel of 70 patients with liver damage to whom tacrolimus had been administered;

FIG. 14 is a graph showing the correlation between the results for the assay of tacrolimus using the homogeneous enzyme immunoassay and using a commercially available immunoassay for tacrolimus for the panel of 70 patients of FIG. 13;

DESCRIPTION

Definitions

Figure 1:
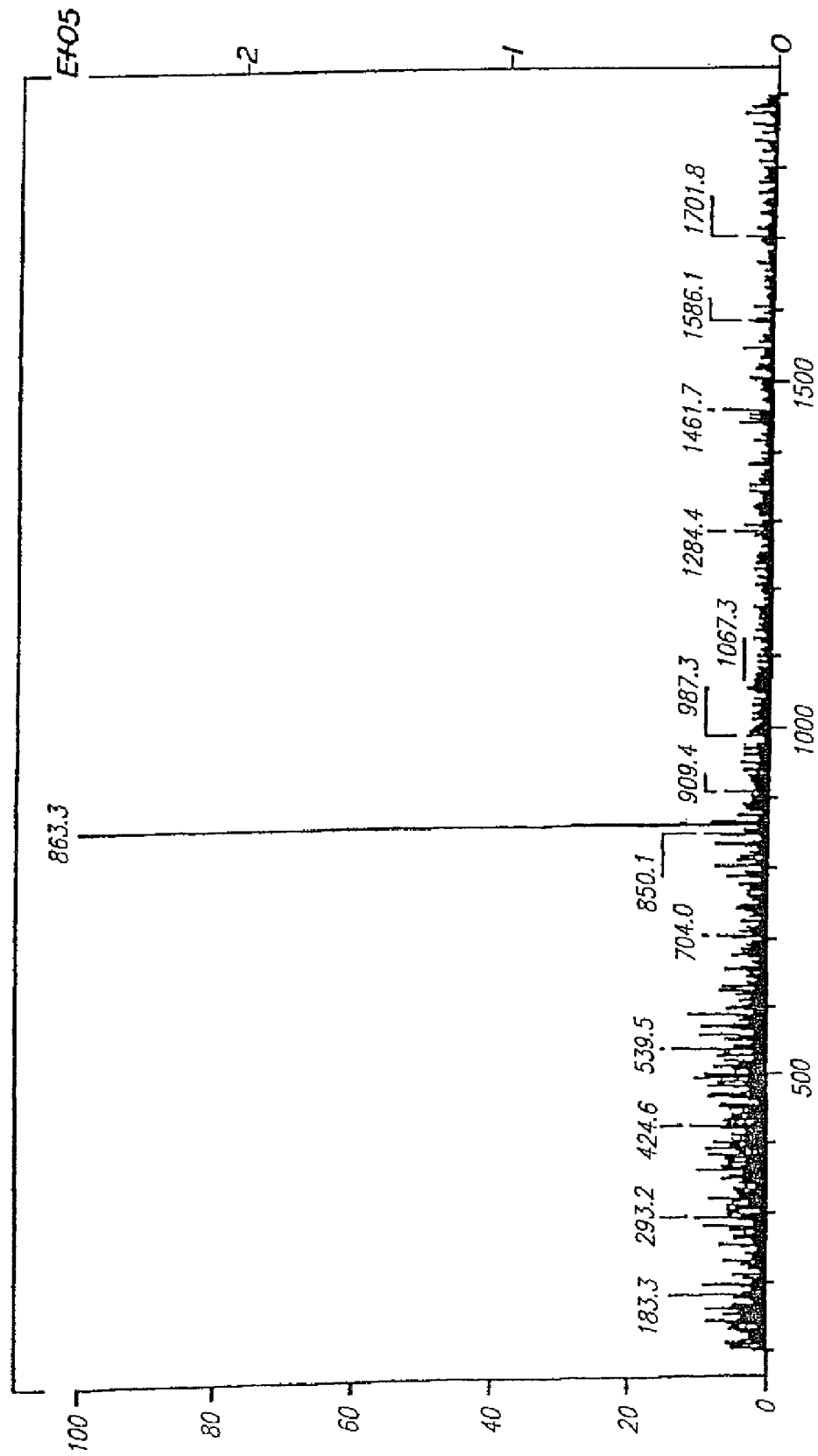
FIG. 1 is a mass spectrogram of the product resulting from the reaction of carboxymethoxylamine with the macrolide antibiotic FK-520, closely related in structure to tacrolimus.

As used herein, the terms defined below have the following meanings unless otherwise indicated:

"Antibody": As used herein the term "antibody" includes both intact antibody molecules of the appropriate specificity, and antibody fragments (including Fab, F(ab'), Fv and F(ab')$_2$), as well as chemically modified intact antibody molecules and antibody fragments, including hybrid antibodies assembled by in vitro association of subunits. Also included are single-chain antibody molecules generally denoted by the term sFv and humanized antibodies in which some or all of the originally non-human constant regions are replaced with constant regions originally derived from human antibody sequences. Both polyclonal and monoclonal antibodies are included unless otherwise specified; in a number of contexts, monoclonal antibodies are specifically specified. Additionally included are modified antibodies or antibodies conjugated to labels or other molecules that do not block or alter the binding capacity of the antibody.

"Nucleic Acid Sequence": The term "nucleic acid sequence" includes both DNA and RNA unless otherwise specified, and, unless otherwise specified, includes both double-stranded and single-stranded nucleic acids. Also included are hybrids such as DNA-RNA hybrids. In particulars reference to DNA includes RNA that has either the equivalent base sequence except for the substitution of uracil in RNA for thymine in DNA, or has a complementary base sequence except for the substitution of uracil for thymine, complementarity being determined according to the Watson-Crick base pairing rules. Additionally, a reference to a nucleic acid sequence includes its complement according to the Watson-Crick base pairing rules unless otherwise specified.

We have developed an improved monoclonal antibody to tacrolimus based on the use of tacrolimus derivatized at a carbon atom within the non-binding domain, preferably carbon-22. Polyclonal antibodies produced by immunization of antibody-producing animals with this immunogen are first made. The resulting antibody-producing cells are then used for cell fusion with a suitable fusion partner to produce hybridomas. The resulting monoclonal antibodies produced by the hybridomas are particularly useful in immunoassays for the detection of tacrolimus.

I. Derivatives of Tacrolimus

Accordingly, one aspect of the present invention is derivatives of tacrolimus derivatized at a carbon atom within the non-binding domain of tacrolimus. Preferably, the derivative is derivatized at the carbon-22 position. One particularly preferred class of derivatives involves reacting the keto group at the 22 position with an amine to produce an oxime. A particularly preferred amine is carboxymethoxylamine. The reaction of tacrolimus with carboxymethoxylamine produces a carboxymethyl oxime.

This reaction involves reacting tacrolimus with carboxymethoxylamine in methanol in the presence of sodium acetate to give the oxime. Accordingly, another aspect of the present invention is a method of derivatizing tacrolimus comprising reacting tacrolimus with carboxymethoxylamine to produce a carboxymethyl oxime derivative of tacrolimus, the oxime moiety being located at carbon-22. Further details of this reaction are given in Example 1.

Accordingly, another aspect of the present invention is a conjugate comprising the derivative of tacrolimus which comprises tacrolimus derivatized with a carboxymethyl oxime moiety at position 22 conjugated to a high molecular weight protein through the oxime moiety. Typically, the high molecular weight protein is a protein that is a suitable carrier for haptens and can be, but is not necessarily limited to, proteins such as bovine serum albumin, thyroglobulin, ovalbumin, fibrinogen, or keyhole limpet hemocyanin. A particularly preferred carrier is keyhole limpet hemocyanin. Alternatively, the high molecular weight protein can be an enzyme, such as an enzyme producing a detectable signal, such as glucose-6-phosphate dehydrogenase or alkaline phosphatase. Such conjugates are particularly useful in immunoassays for tacrolimus, as discussed below.

The preparation of these conjugates is set out in more detail below in Example 2. In general however, a method of preparation of the conjugate of tacrolimus with the high molecular weight protein is as follows: (1) preparation of the carboxymethyl oxime of tacrolimus as described above; (2) activating the carboxymethyl oxime to produce a reactive N-hydroxysuccinimide ester; and (3) reacting the N-hydroxysuccinimide ester with the high molecular weight protein to produce the conjugate. This reaction is discussed in detail in Example 2. The activation of the carboxymethyl oxime to produce the N-hydroxysuccinimide ester typically is performed using a coupling agent such as a water-soluble carbodimide. A preferred water-soluble carbodiimide is –3-(3-dimethylaminopropyl 1-ethyl-3-dimethylaminopropyl)-carbodiimide hydrochloride (EDAC). Other water-soluble carbodiimides are known in the art and can also be used.

In addition to forming conjugates with high molecular weight proteins such as keyhole limpet hemocyanin, the present invention also encompasses derivatives of tacrolimus substituted with a carboxymethyl oxime moiety at carbon 22 linked through a linker to a biotin moiety. The linker can take one of a number of forms and can have different lengths. The use of linkers between biotin and a hapten or antigen is well known in the art and need not be described further in detail here. In one particularly preferred derivative, the linker has the structure $NH_2$—$CH_2$—$CH_2$—NH—CO—$(CH_2)_5$—$NH_2$. One of the amine groups of the linker forms an amide bond with the carboxyl group of the carboxymethyl oxime, and the other amine group forms an amide bond with the carboxyl group of the biotin.

The length of this spacer can be changed by inserting or deleting one or more $CH_2$ (methylene) groups at the two places in the spacer that have 2 or more methylene groups.

The derivatives can be formed by reacting a N-hydroxysuccinimide ester as described above with the carboxyl group of biotin or a biotin derivative or analogue. This reaction can be performed as described above.

In general, the method of forming such biotin derivatives comprises:

(1) reacting tacrolimus with carboxymethoxylamine to produce a carboxymethyl oxime derivative of tacrolimus, the carboxymethyl oxime derivative being located at position 22;

(2) activating the carboxymethyl oxime to produce a reactive N-hydroxysuccinimide ester; and (3) reacting the N-hydroxysuccinimide ester with the carboxyl group of biotin or a biotin derivative or analogue.

In one preferred alternative, as discussed below in Example 3, the oxime is reacted with EDAC and N-hydroxysuccinimide in dimethylformamide (DMF). The activated product is then reacted with the biotin containing the linker, such as LC-biotin.

Still another embodiment of conjugates of tacrolimus derivatized at a carbon atom within the non-binding domain of tacrolimus, preferably position 22, is a bromoacetyl derivative. The preparation of bromoacetyl derivatives of tacrolimus derivatized at position 22 is described in Example 4. In general, the preparation of such derivatives comprises:

(1) reacting tacrolimus with carboxymethoxylamine to produce a carboxymethyl oxime derivative of tacrolimus, the carboxymethyl oxime derivative being located at position 22;

(2) activating the carboxymethyl oxime to produce a reactive N-hydroxysuccinimide ester; and (3) reacting the N-hydroxysuccinimide ester with the trifluoroacetic acid salt of bromoacetyl ethylenediamine to produce a bromoacetyl derivative.

The carboxymethyl oxime derivative used in this method is prepared as described above.

Such bromoacetyl derivatives can be used to produce enzyme conjugates of tacrolimus by reacting the bromoacetyl moiety with a sulfhydryl group of an enzyme, such as a mutein of glucose 6-phosphate dehydrogenase that contains a cysteine residue. The bromoacetyl derivative can react with other cysteine groups in other enzymes or proteins to produce other enzyme or protein conjugates of tacrolimus.

II. Monoclonal and Polyclonal Antibodies and Hybridomas

Another aspect of the present invention is monoclonal antibodies and hybridomas producing them, as well as polyclonal antibodies produced by immunization of antibody-producing animals with tacrolimus derivatives as described above.

One preferred embodiment of a monoclonal antibody to the present invention is a murine monoclonal antibody to tacrolimus that is a $IgG_1\lambda$ monoclonal antibody designated 1H6. This monoclonal antibody reacts with 13-demethyl tacrolimus but has less than about 8% cross-reactivity to all of the following tacrolimus metabolites: 15-demethyl tacrolimus; 31-demethyl tacrolimus; 13,31-didemethyl tacrolimus; 15,31-didemethyl tacrolimus; and 12-hydroxy tacrolimus. This monoclonal antibody has an estimated affinity for binding to tacrolimus of $3.7 \times 10^9$ liters/mole.

Another monoclonal antibody according to the present invention is a monoclonal antibody to tacrolimus that: (1)

competes with the IgG₁λ monoclonal antibody designated 1H6 at least about 80% as effectively on a molar basis as compared with the IgG₁λ monoclonal antibody designated 1H6 as measured by competition assays; and (2) has less than about 10% cross reactivity with each of the following tacrolimus metabolites: 15-demethyl tacrolimus; 31-demethyl tacrolimus; 13,31-didemethyl tacrolimus; 15,31-didemethyl tacrolimus; and 12-hydroxy tacrolimus.

Preferably, the monoclonal antibody competes at least about 90% as effectively on a molar basis as the monoclonal antibody designated 1H6 and has less than about 8% cross reactivity with each of these tacrolimus metabolites.

Another aspect of the present invention is a hybridoma producing a monoclonal antibody as described above. This includes a hybridoma producing the IgG₁λ monoclonal antibody to tacrolimus designated as 1H6. This also includes a hybridoma producing a monoclonal antibody as described above which competes at least about 80% as effectively on a molar basis with that antibody and has a limited degree of cross-reactivity with tacrolimus metabolites as described above.

Another embodiment of the present invention is humanized monoclonal antibodies. In some applications it is preferred to have humanized monoclonal antibodies in which at least some of the constant regions of the antibody are replaced by human constant regions so that the monoclonal antibody is humanized. Typically, such procedures involve the grafting of the murine complementarity-determining regions (CDRs) onto a human antibody. Additional alterations of individual amino acids within the framework may be necessary to recreate the antigen-binding site. Typically, this technique involves amplification of cDNA for the heavy and light variable chains of the murine hybridoma using the polymerase chain reaction (PCR) with a subset of synthetic oligonucleotide primers with a small level of degeneracy. Mutagenesis, if required, can be carried out by standard methods. Typically, humanized V genes carrying the variable regions are cloned into suitable expression vectors and expressed in cells such as COS cells or CHO-K1 cells. Other mutations can be made as needed. The preparation of such humanized monoclonal antibodies is generally known in the art and is described, for example in C. A. K. Borrebaeck, "Antibody Engineering" 2d. ed., Oxford University Press, New York, 1995), incorporated herein by this reference.

Therefore, another embodiment of the present invention is a single-chain recombinant antibody (sFv) including therein the variable regions of an antibody to tacrolimus that: (1) competes with the IgG₁λ monoclonal antibody designated 1H6 and described above at least about 80% as effectively on a molar basis as compared with the IgG₁λ monoclonal antibody designated 1H6 as measured by competition assays; and (2) has less than about 10% cross-reactivity with each of 15-demethyl tacrolimus, 31-demethyl tacrolimus, 13,31-didemethyl tacrolimus, 15,31-didemethyl tacrolimus, and 12-hydroxy tacrolimus.

Strategies for producing sFv single-chain antibodies are well known in the art and are described, for example, in C. A. K. Borrebaeck, "Antibody Engineering," supra, incorporated herein by this reference. In general, constructing an sFv involves manipulation of heavy- and light-chain variable regions, which must be connected at the gene level by an oligonucleotide sequence of codons for an appropriate peptide linker. The linker must connect the $V_H$ and $V_L$ domains of the chosen Fv without perturbing interdomain contacts or interfering with domain folding. A typically used linker is a 15-residue peptide that consists of 3 repeating units, each of which has four glycine residues followed by a serine residue (J. S. Huston et al. "Protein Engineering of Antibody Binding Sites: Recovery of Specific Activity in an Anti-Digoxin Single-Chain Fv Analog Produced in *Escherichia coli*," *Proc. Natl. Acad. Sci. USA* 85:5879-5883 (1988)). Typically, such single-chain antibodies are produced in inclusion bodies in bacteria. Activity typically requires refolding of the expressed polypeptides from inclusion bodies; conditions for performing this are generally well known.

Accordingly, such single-chain antibodies or sFv are also within the scope of the present invention.

Another embodiment of the present invention is a monoclonal antibody to tacrolimus produced by fusion of antibody-producing cells from an antibody-producing mammal immunized with tacrolimus derivatized with a carboxymethyl oxime moiety at a carbon atom in the non-binding domain of tacrolimus conjugated to a high molecular weight protein with a suitable fusion partner. Preferably, the carbon atom in the non-binding domain of tacrolimus is carbon 22. As indicated above, typically, the high molecular weight protein used for immunization is keyhole limpet hemocyanin.

The preparation of monoclonal antibodies is well known in the art and need not be described further here. For example, the production of monoclonal antibodies is described in J. W. Goding, "Monoclonal Antibodies: Principles and Practice" (2d. ed., Academic Press, London, 1986), incorporated herein by this reference.

In general, the first step in the procedure is the production of polyclonal antibodies by standard techniques, such as immunization of an antibody-producing animal such as a mouse, a rat, a goat, a sheep, or a cow with the antigen. The antigen is typically coupled to a high molecular weight carrier such as a high molecular weight protein as discussed above. Immunization can be performed with or without an adjuvant such as complete Freund's adjuvant or other adjuvants such as monophosphoryl lipid A and synthetic trehalose dicorynomycolate adjuvant; it is generally preferred to immunize with an adjuvant. The next step is to isolate spleen cells from antibody-producing animals and fuse the antibody-producing spleen cells with an appropriate fusion partner, typically a myeloma cell, such as by the use of polyethylene glycol or other techniques. Typically, the myeloma cells used are those that grow normally in hypoxanthine-thymidine (HT) medium but cannot grow in hypoxanthine-aminopterin-thymidine (HAT) medium, used for selection of the fused cells. The next step is selection of the fused cells, typically by selection in HAT medium. The next step is to screen the cloned hybrids for appropriate antibody production using immunoassays such as enzyme-linked immunosorbent assay (ELISA) or other immunoassays appropriate for screening. Again, these steps are well known in the art and need not be described in further detail.

Another embodiment of the present invention is an antibody, which can be polyclonal antibody, to tacrolimus produced by immunization of an antibody-producing mammal with tacrolimus derivatized with a carboxymethyl oxime moiety at a carbon atom in the non-binding domain of tacrolimus conjugated to a high molecular weight protein as described above. Preferably, the carbon atom in the non-binding domain of tacrolimus is carbon 22.

Another aspect of the present invention is a conjugate comprising an antibody of the present invention as described above conjugated directly or indirectly to a detectable label. The antibody can be conjugated directly to the detectable label so that a covalent link exists between the label and the antibody. Such methods are well known in the art; such techniques are described, for example, in G. T. Hermanson, "Bioconjugate Techniques" (Academic Press, San Diego, 1996), incorporated herein by this reference. In general, such techniques link reactive groups on the antibody and the label, typically through a linker or spacer. The length of the linker or spacer can be adjusted to preserve the activity and specificity of the antibody and to ensure that the label produces the detectable signal without interfering with the activity of the antibody.

Such labels are well known in the art and need not be described in detail. Such labels can include, but are not limited to, an enzyme label, a radioactive label, a fluorescent label, a chemiluminescent label, a bioluminescent label, or a particulate label.

Enzyme labels are well known in the art. Typically, the enzyme used is one that produces a visually detectable signal such as a colored product or an insoluble product. Among the enzymes that can be used are horseradish peroxidase, β-galactosidase, alkaline phosphatase, glucose oxidase, urease, catalase, lysozyme, malate dehydrogenase, glucose-6-phosphate dehydrogenase, and ribonuclease A. Other enzymes that can be used for immunoassays are well known in the art.

Among the particulate labels that can be used are latex labels and colloidal metal labels such as colloidal gold, silver, tin, and other metals.

A large variety of radioactive, fluorescent, chemiluminescent, and bioluminescent labels are known in the art. These labels need not be described further here.

As an alternative to a direct covalent linkage between the antibody and the label, the linkage can be indirect such as through a biotin-avidin linkage. The binding of biotin to avidin or its bacterial analog streptavidin is well understood in the art. This binding is highly specific and has an extremely high affinity. Typically, the antibody is conjugated to a biotin moiety and the label is bound to avidin or streptavidin. Other arrangements can also be used. The use of an avidin-biotin linkage is described, for example, in G. T. Hermanson, supra, pp. 570-592.

III. Immunoassays

Another aspect of the present invention is immunoassays for tacrolimus using the antibodies described above. In general, such an immunoassay is a method of detecting or determining tacrolimus. The term "detecting" is used herein to refer to a qualitative assay that detects the presence or absence of tacrolimus in a sample, while the term "determining" refers to a quantitative or semiquantitative assay that determines the concentration of tacrolimus in the sample.

In general, such an immunoassay method comprises the steps of:
(1) providing a sample suspected of containing tacrolimus;
(2) reacting the sample with:
  (a) an antibody against tacrolimus as described above; and
  (b) optionally, with a tacrolimus analogue; wherein one of the antibody or the tacrolimus analog is labeled with a label producing a detectable signal; and
(3) observing or measuring one of:
  (a) a signal associated with tacrolimus bound to antibody;
  (b) a signal associated with tacrolimus unbound to antibody; or
  (c) total signal present to detect or determine the presence or concentration of tacrolimus in the sample.

Such assays are described as either homogeneous or heterogeneous. In a heterogeneous assay, the antibody bound to antigen is separated from antibody unbound to antigen. This separation can be done by a number of steps well known in the art, such as differential solubility, reactivity with another antibody, or other properties. Such assays are well known in the art and need not be described further in detail here. If either the signal associated with tacrolimus bound to antibody or the signal associated with tacrolimus unbound to antibody is to be detected or determined, a heterogeneous assay is performed. By contrast, in a homogeneous assay, the total signal present is detected or determined. In a homogeneous assay, the existence of an antigen-antibody complex modulates the signal so that the signal level changes without a requirement of separating antigen bound to antibody from antigen unbound to antibody.

Although many heterogeneous immunoassay formats are well known in the art, in the context of the present invention, it is generally preferred to use a homogeneous immunoassay system. An example of a preferred homogeneous immunoassay system for the immunoassay of tacrolimus using antibodies according to the present invention is the homogeneous assay system known as EMIT, as described in D. D. Schottelius, "Homogeneous Immunoassay System (EMIT) for Quantitation of Antiepileptic Drugs in Biological Fluids" in *Antiepileptic Drugs: Quantitative Analysis and Interpretation* (C. E. Pippenger et al., Raven Press, New York, 1978, Ch. 10, pp: 98-101, incorporated herein by this reference, and further described in U.S. Pat. No. 3,817,837 to Rubenstein et al., incorporated herein by this reference.

In general, in this assay, an enzyme such as glucose-6-phosphate dehydrogenase is conjugated to the analyte (here, tacrolimus) to be assayed in such a fashion that it does not significantly alter the activity of the enzyme. However, when this analyte-enzyme conjugate is bound to the antibody for the analyte, the configuration is such that the active site of the enzyme is blocked and thus excludes the substrate. This results in the enzyme activity being reduced. When the complex is not bound, the active site is available to interact with the substrate. If free analyte is present in the unknown sample, the free analyte then binds to the antibody. This prevents the binding of the analyte-enzyme conjugate and decreases the antibody-induced in activation of the enzyme activity in proportion to the concentration of analyte in the sample. Thus, in such a homogeneous assay, the greater the concentration analyte in the sample, the greater the signal produced by the enzyme label. This is a homogeneous assay as described above.

IV. Test Kits

Another aspect of the present invention is a test kit, particularly for use in the EMIT homogeneous immunoassay described above.

Such a test kit comprises, packaged in separate containers:
(1) an antibody as described above; and
(2) a tacrolimus analogue labeled directly or indirectly with an enzyme label.

The tacrolimus analogue can be labeled either directly or indirectly; it is generally preferred that the tacrolimus analogue is labeled indirectly with a biotinylated tacrolimus molecule and a streptavidinylated enzyme. However, the tacrolimus can be coupled at carbon 22 with an enzyme suitable for use in the EMIT assay as described above.

Test kits can also include, in separately packaged containers, other ingredients such as substrates, buffers, stabilizers, coenzymes, and other ingredients required for the performance of the immunoassay.

The invention is illustrated by the following Examples. The Examples are for illustrative purposes only and are not intended to limit the invention.

EXAMPLES

Example 1

Preparation of Carbon-22-Substituted Derivatives of Tacrolimus

To determine the feasibility of derivatizing tacrolimus at carbon 22, as a model for this molecule, derivatization of the closely related molecule FK-520 was performed. FK-520 has the same structure as tacrolimus except that is has an ethyl instead of an allyl group at carbon 21.

Figure 2:
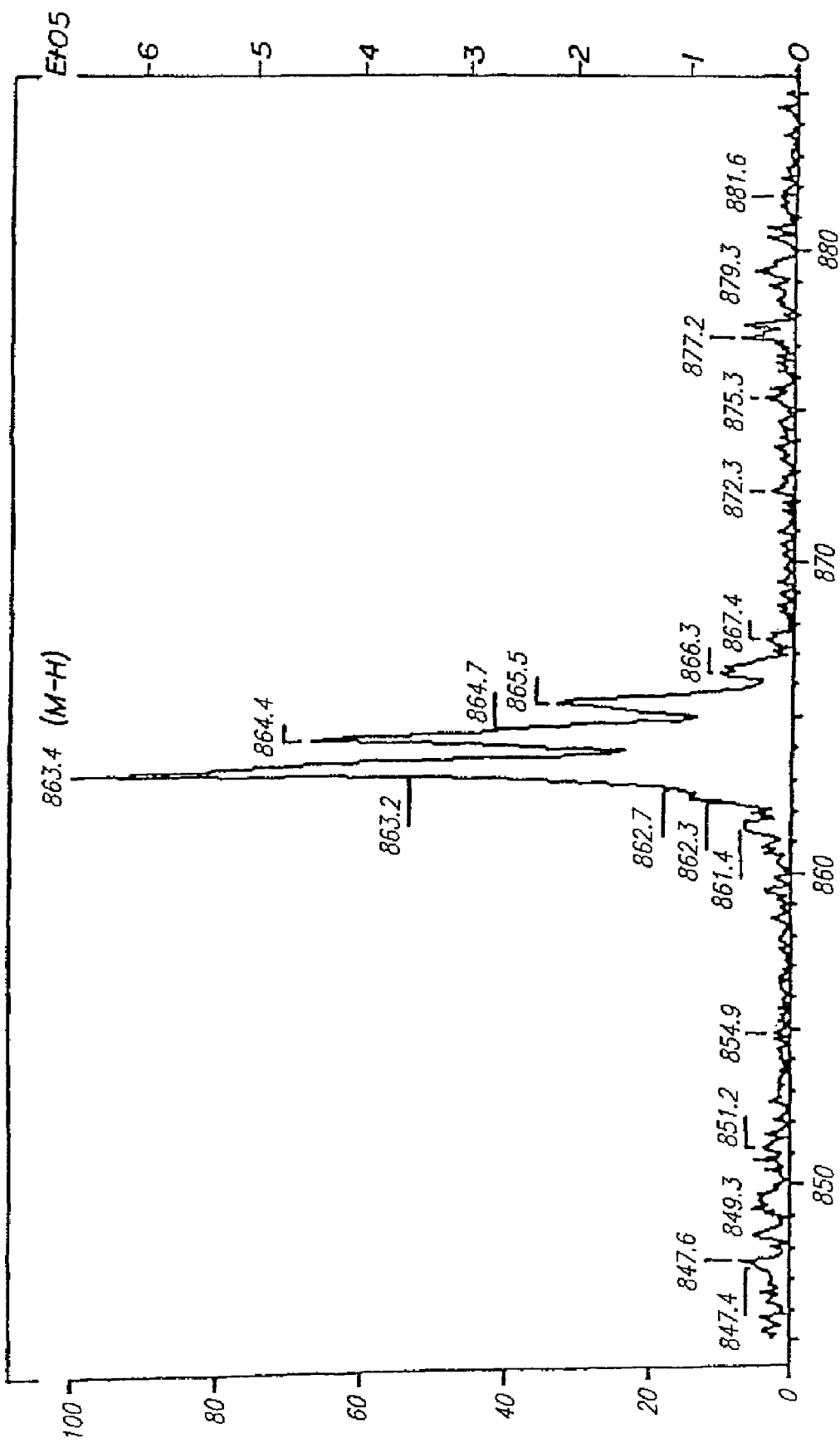
FIG. 2 is a portion of the mass spectrogram of FIG. 1, shown in expanded resolution centered around the predominant peak.

For these experiments, reagents and solvents were commercial grades and were used as supplied without further purification. The reaction with FK-520 on a small scale (0.9 mg) was performed as follows: To a solution of FK-520 (0.9 mg, 1.1 µmol) in 0.23 mL of methanol was added sodium acetate (1.5 mg, 18.3 µmol, 16 equiv.) and carboxymethoxylamine hydrochloride (3.0 mg, 13.7 µmol, 12 equiv.). The reaction was stirred at room temperature for 3 hours under argon. Solvent was then evaporated by purging with a stream of argon. Thin layer chromatography in 5:6:1.1:0.5% ($CH_2Cl_2$/EtOAc/MeOH/OAc) on plates from Analtech (scored 10×20 cm, 250 microns) of the residue afforded 2 geometric isomers of FK-520 mono-oximes, enough to be analyzed by fast atom bombardment mass spectroscopy. LSIMS of $C_{45}H_{72}N_2O_{14}$ would be expected to give a $[M–H]^-$ of 863.3. The relevant portions of the mass spectroscopy results are shown in FIGS. 1 and 2. FIG. 2 is an portion of the spectrum shown in FIG. 1 expanded around the central peak.

Subsequently an analogous procedure was used to prepare the monooxime of tacrolimus. Tacrolimus was provided as a solid mixture in a capsule containing 1.02 mg of tacrolimus monohydrate and approximately a 6-fold excess of sodium dodecyl sulfate (SDS). The solid mixture from 30 capsules was combined and extracted 4 times with 12 ml each time of ethyl acetate. The combined organic extracts were concentrated under a vacuum to give 49 mg of crude tacrolimus which was used directly in the following reaction.

Figure 3:
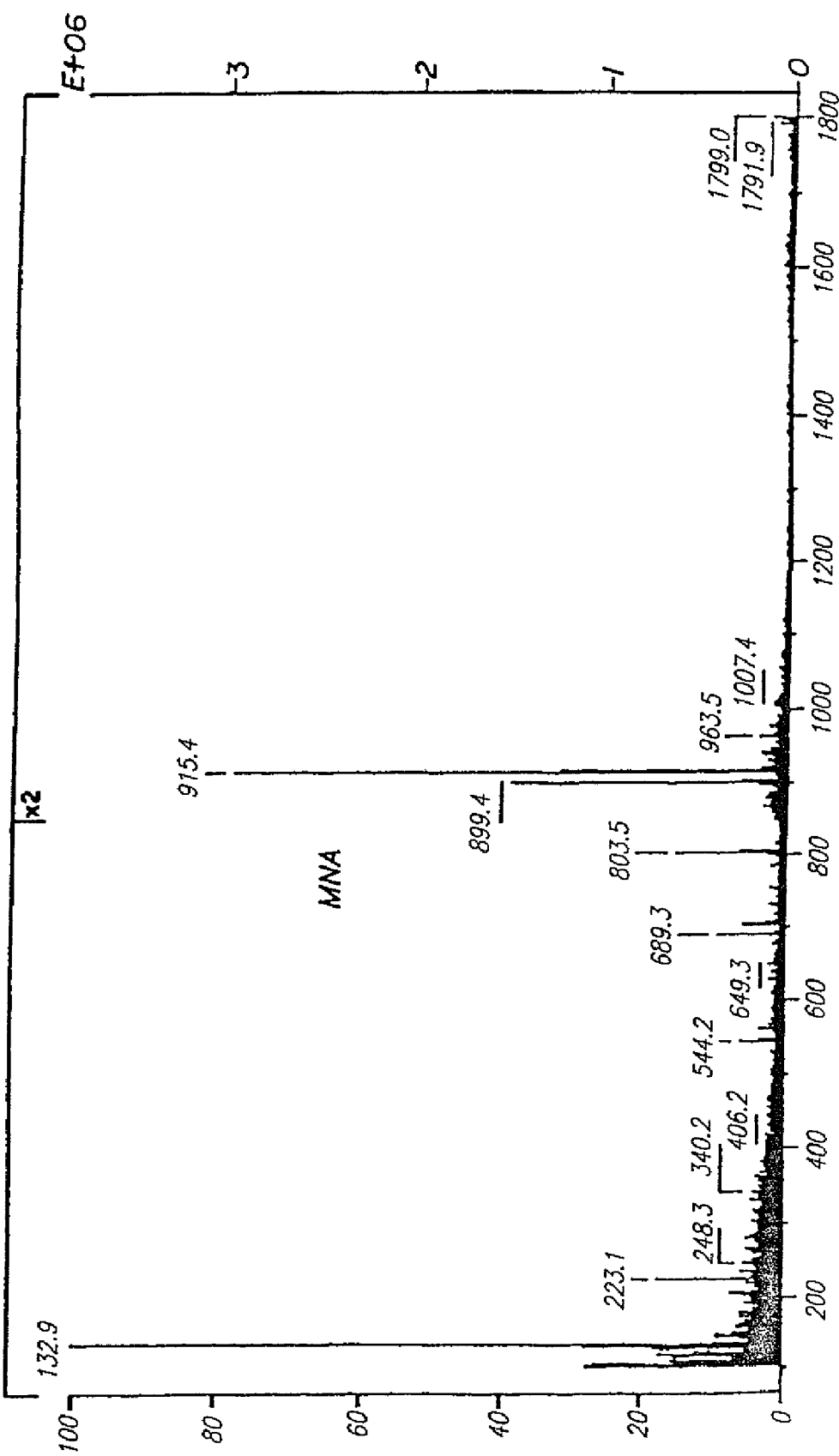
FIG. 3 is a mass spectrogram of the product resulting from the reaction of carboxymethoxylamine with tacrolimus.
Figure 4:
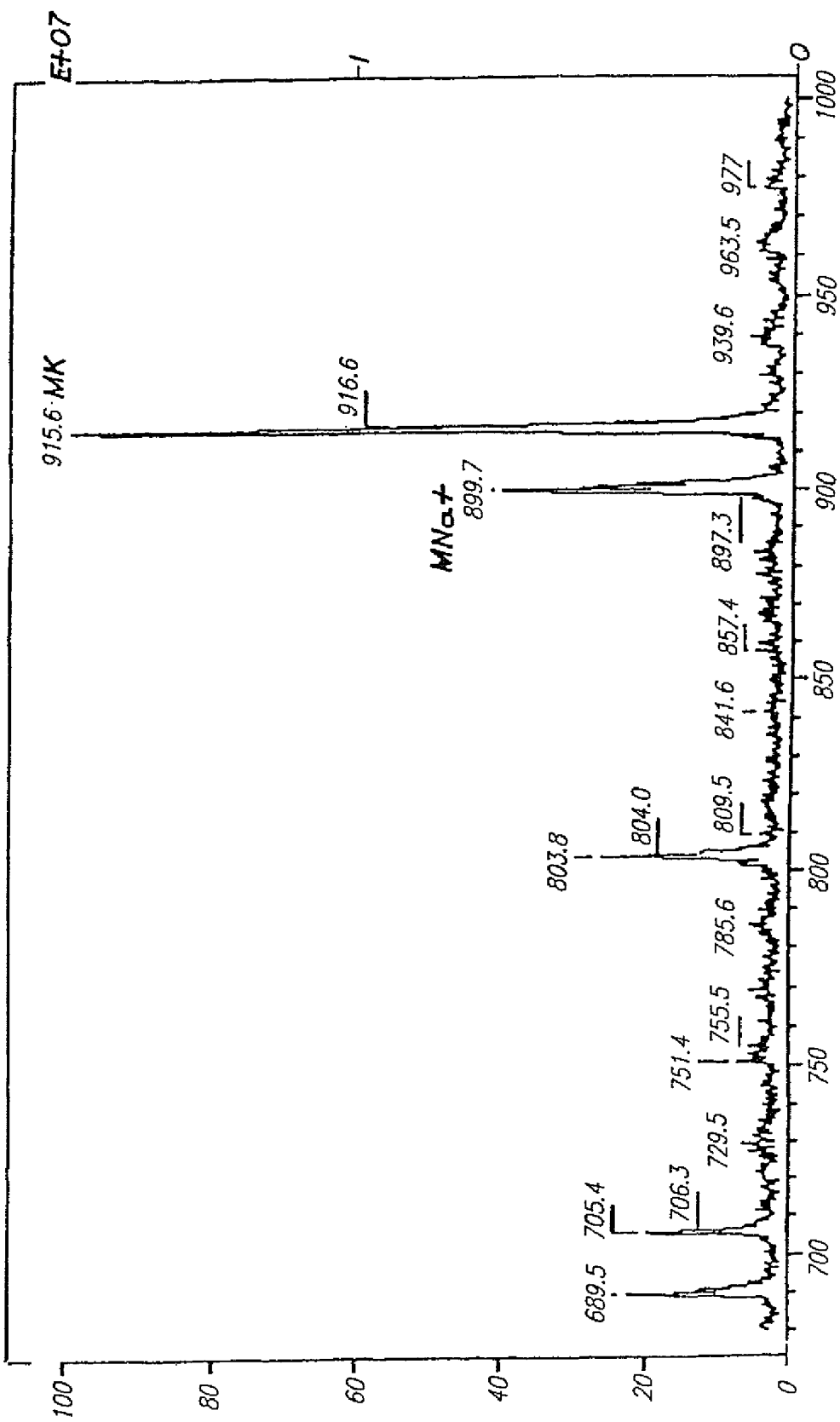
FIG. 4 is a portion of the mass spectrogram of FIG. 3, shown in expanded resolution centered around the predominant peak.

To the 49 mg of crude tacrolimus (theoretically 36.5 µmol) in 3.5 ml of methanol was added sodium acetate (16.7 mg, 204 µmol, 5.6 equiv.), and carboxymethoxylamine hydrochloride (40 mg, 183 µmol, 5 equiv.). The reaction was stirred at room temperature for 12 hours under argon. Solvent and volatile materials were removed at reduced pressure to give crude solid residue. Preparative thin layer chromatography on pre-coated silica gel plates from Analtech (20×20 cm, 1000 microns) with 30:70:11:0.6 ($CH_2Cl_2$/EtOAc/MeOH/HOAc) of the crude product afforded geometric isomers of tacrolimus monooximes at white solid. LSIMS on $C_{46}H_{72}N_2O_{14}$ was expected to yield 899.4 as $[M+Na]^+$ and 915.4 as $[N+K]^+$. Results are shown in FIGS. 3 and 4. FIG. 4 represents the data of FIG. 3 at higher resolution centered around the relevant portion of the spectrum.

Figure 5:
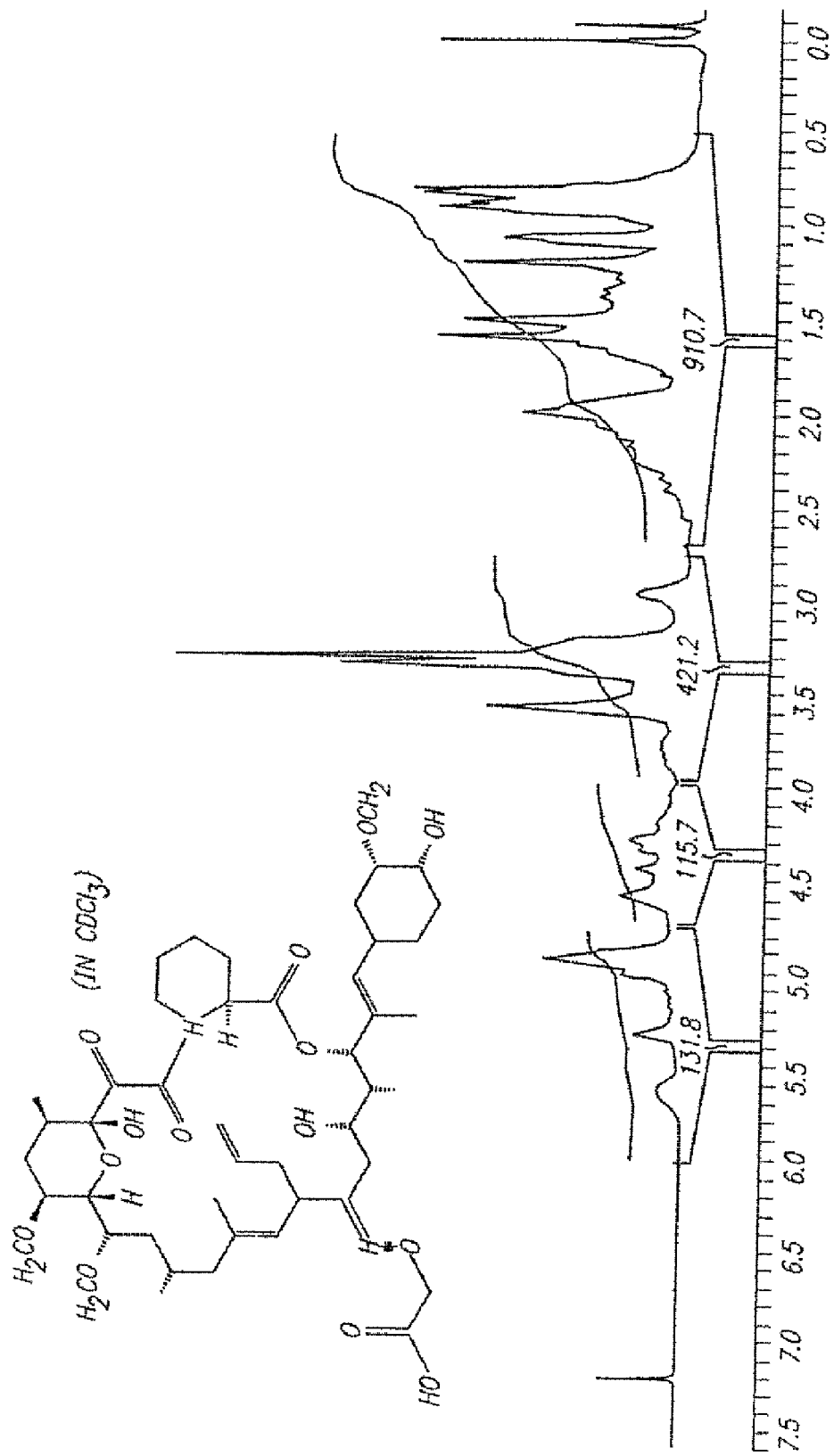
FIG. 5 is a $^1$H NMR spectrum at 250 MHz in CDCl$_3$ of the product resulting from the reaction of carboxymethoxylamine with tacrolimus.
Figure 6:
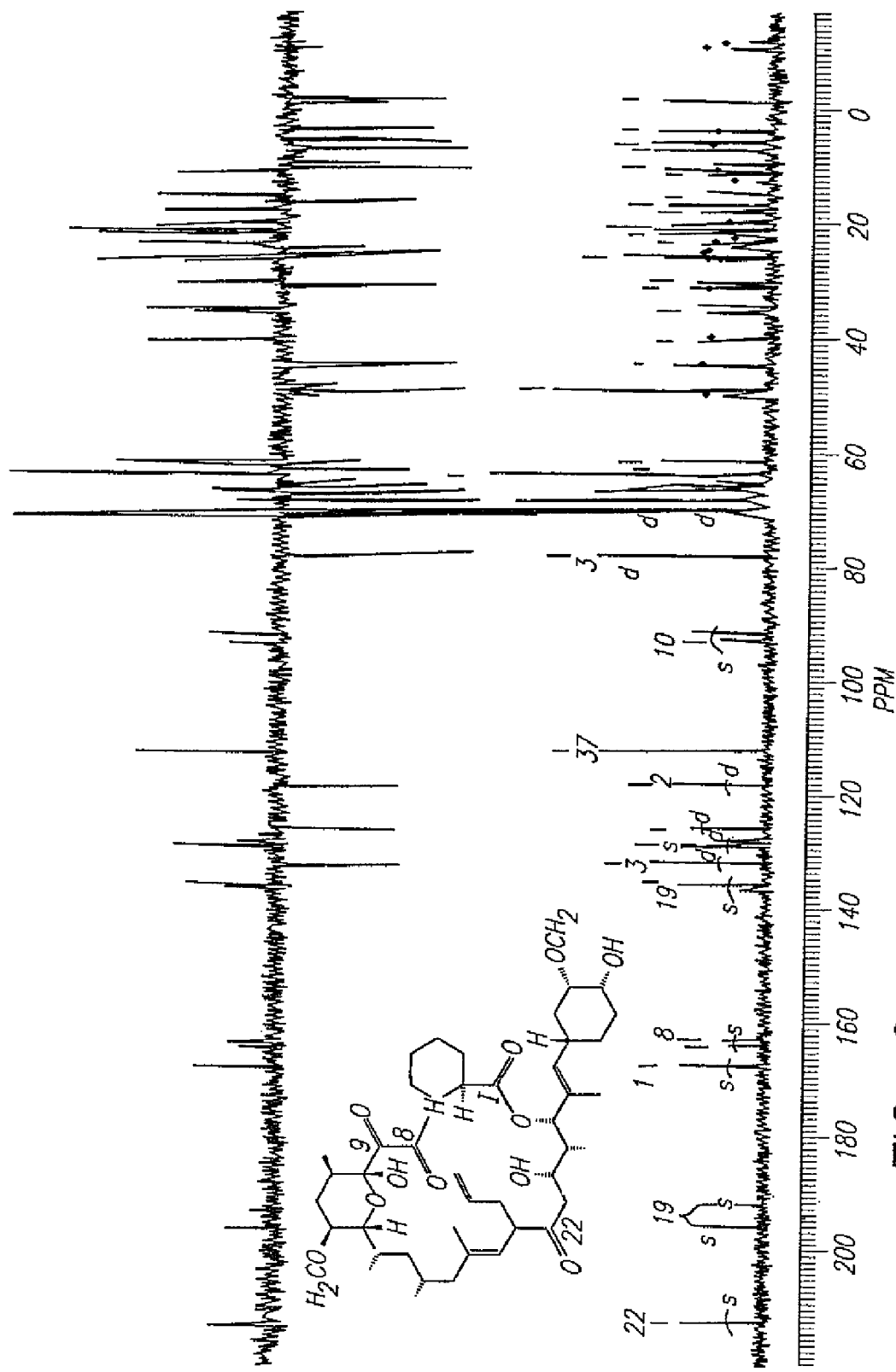
FIG. 6 is a $^{13}$C NMR spectrum at 250 MHz in CDCl$_3$ of the product resulting from the reaction of carboxymethoxylamine with tacrolimus.
Figure 7:
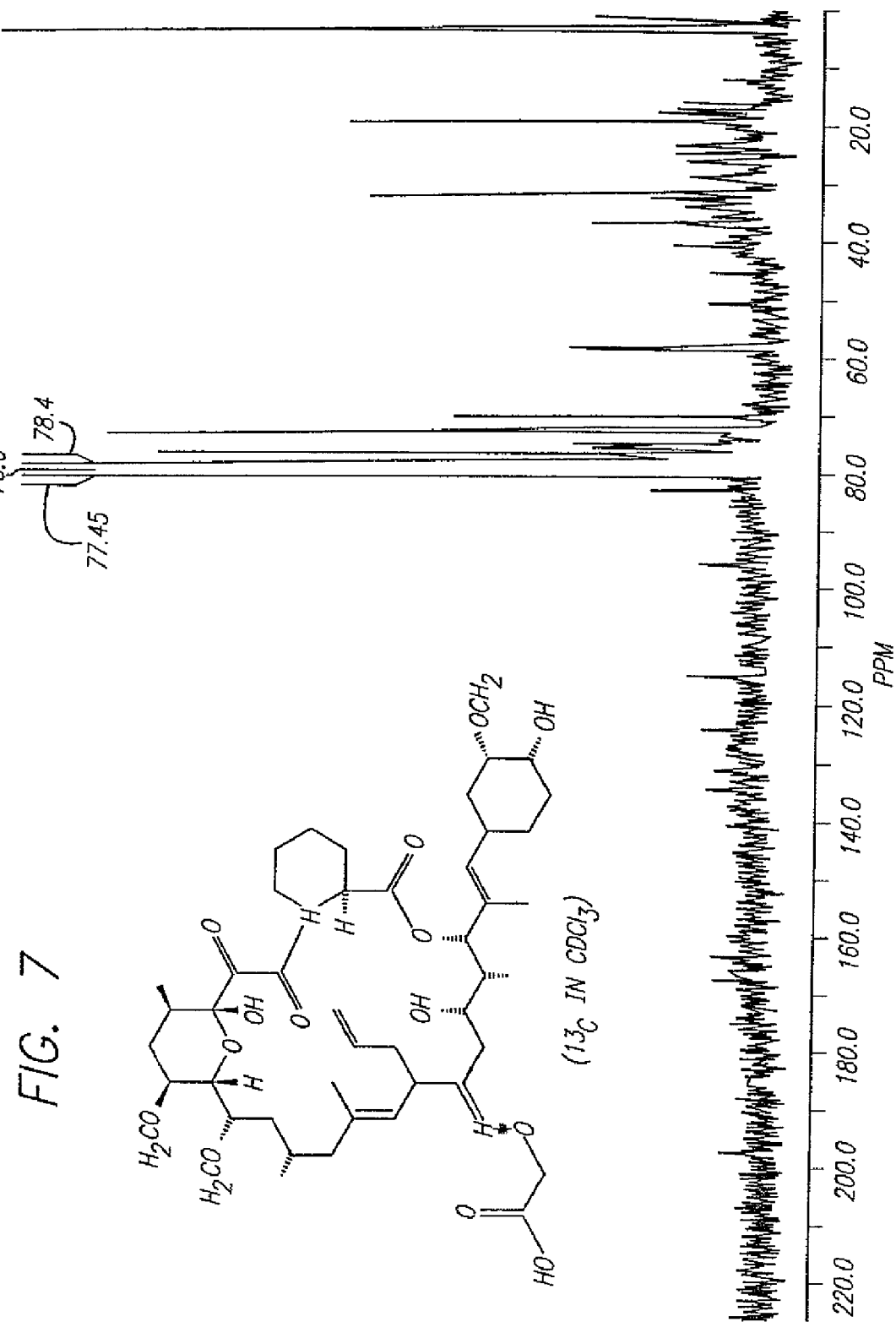
FIG. 7 is a $^{13}$C NMR spectrum at 500 MHz in CDCl$_3$ of tacrolimus shown as a reference.

$^1$H NMR at 250 MHz in $CDCl_3$ of the product of the reaction of carboxymethoxylamine hydrochloride with tacrolimus is shown in FIG. 5. $^{13}$C NMR at 250 MHz in $CDCl_3$ of the product of the reaction of carboxymethoxylamine hydrochloride with tacrolimus is shown in FIG. 6. $^{13}$CNMR at 500 MHz in $CDCl_3$ shown in FIG. 7 was that of tacrolimus as a reference (i.e. underivatized tacrolimus). All NMR spectra were recorded on Bruker instruments.

Example 2

Preparation of Tacrolimus-Keyhole Limpet Hemocyanin Conjugate

To a solution of tacrolimus monooxime (32.3 mg, 36.8 µmol) in 1.05 mL of anhydrous dimethylformamide was added 1-ethyl-3-(3-dimethylaminopropyl)carbodiimide hydrochloride (EDAC) (11 mg, 57.4 µmol, 1.5 equiv.) and N-hydroxysuccinimide (7.3 mg, 63.4 µmol, 1.7 equiv.). The reaction was stirred at room temperature for 1 hour under argon. The mixture was then added dropwise via a syringe to a solution of keyhole limpet hemocyanin (74 mg, 54% pure) in 5.0 mL of phosphate buffered saline (0.1 M, pH 8.0) and 0.25 mL of dimethylformamide. After stirring at room temperature for 2 hours, the resulting suspension was dialyzed (1×4 L, 4° C., 2 h) against PBS (10 mM, pH 7.0).

The resulting mixture was then extracted 3× with $CH_2Cl_2$ to remove any trace amount of unreacted tacrolimus monooximes. Quantitative analysis of the mixture was conducted using bicinchoninic acid (BCA) protein assay solution to give 50 mg of immunogen in 8 ml of PBS (10 mM, pH 7.0).

Determination of the hapten number using the TNBS method (A. F. S. A. Habeeb, *Anal. Biochem.* 14:328 (1966)) gave a hapten number of 1300. The immunogen was immediately frozen using a dry ice-acetone bath and kept at −20° C. for storage.

Example 3

Preparation of Tacrolimus-Biotin Conjugate

Figure 8:
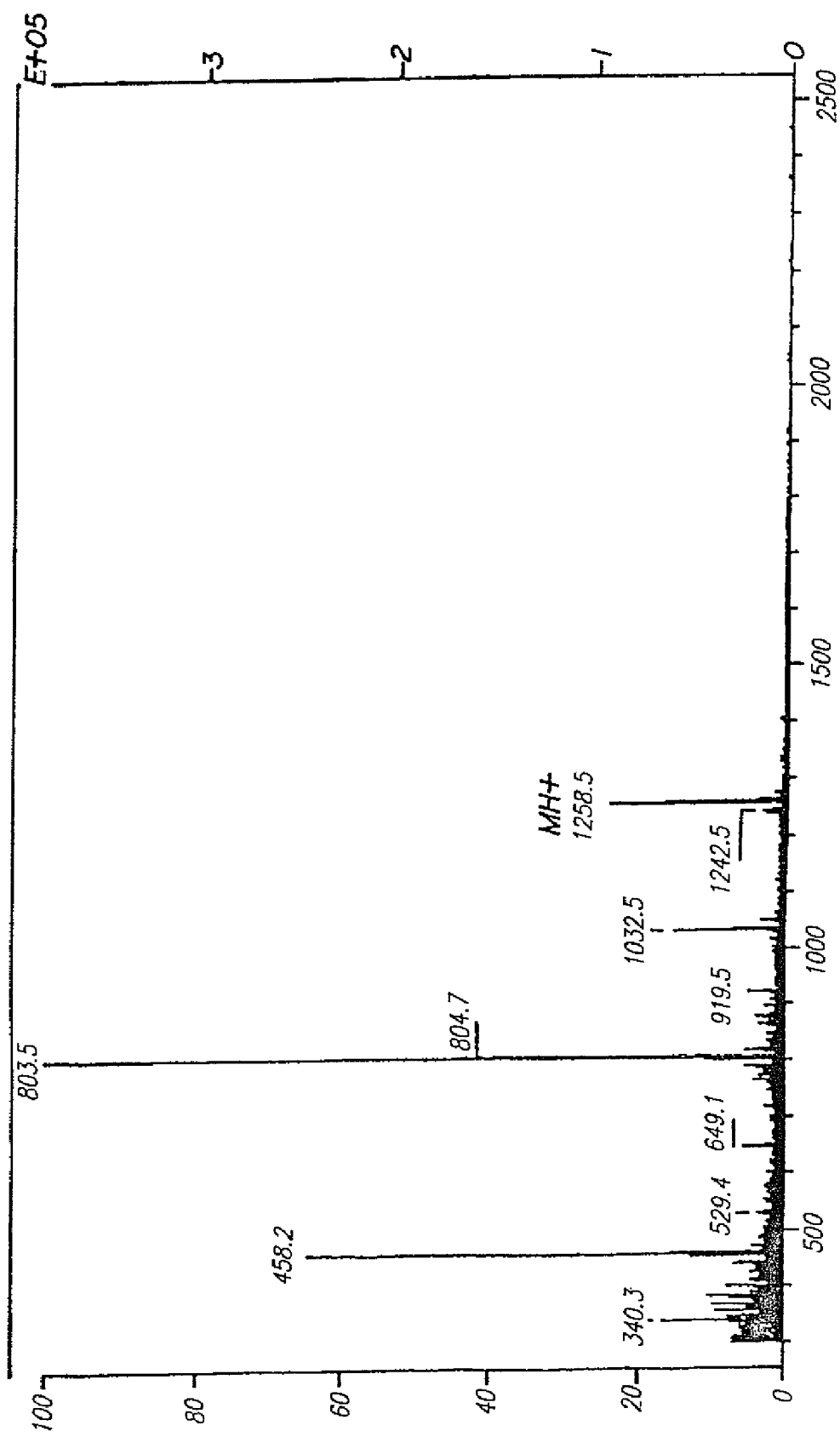
FIG. 8 is a mass spectrogram of the product resulting from the reaction of LC-biotin with tacrolimus monooxime.
Figure 9:
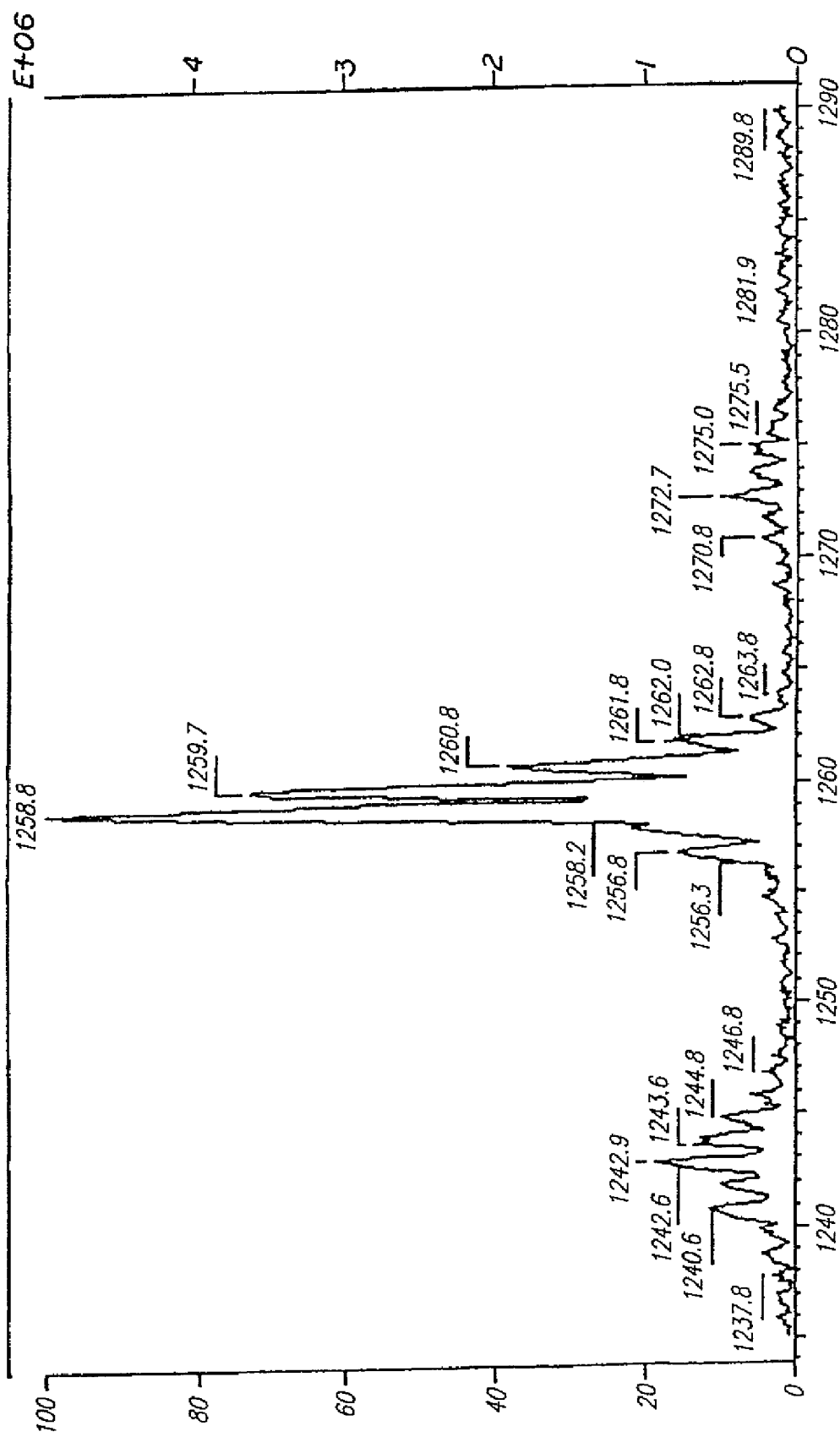
FIG. 9 is a portion of the mass spectrogram of FIG. 8, shown in expanded resolution centered around the predominant peak.
Figure 10:
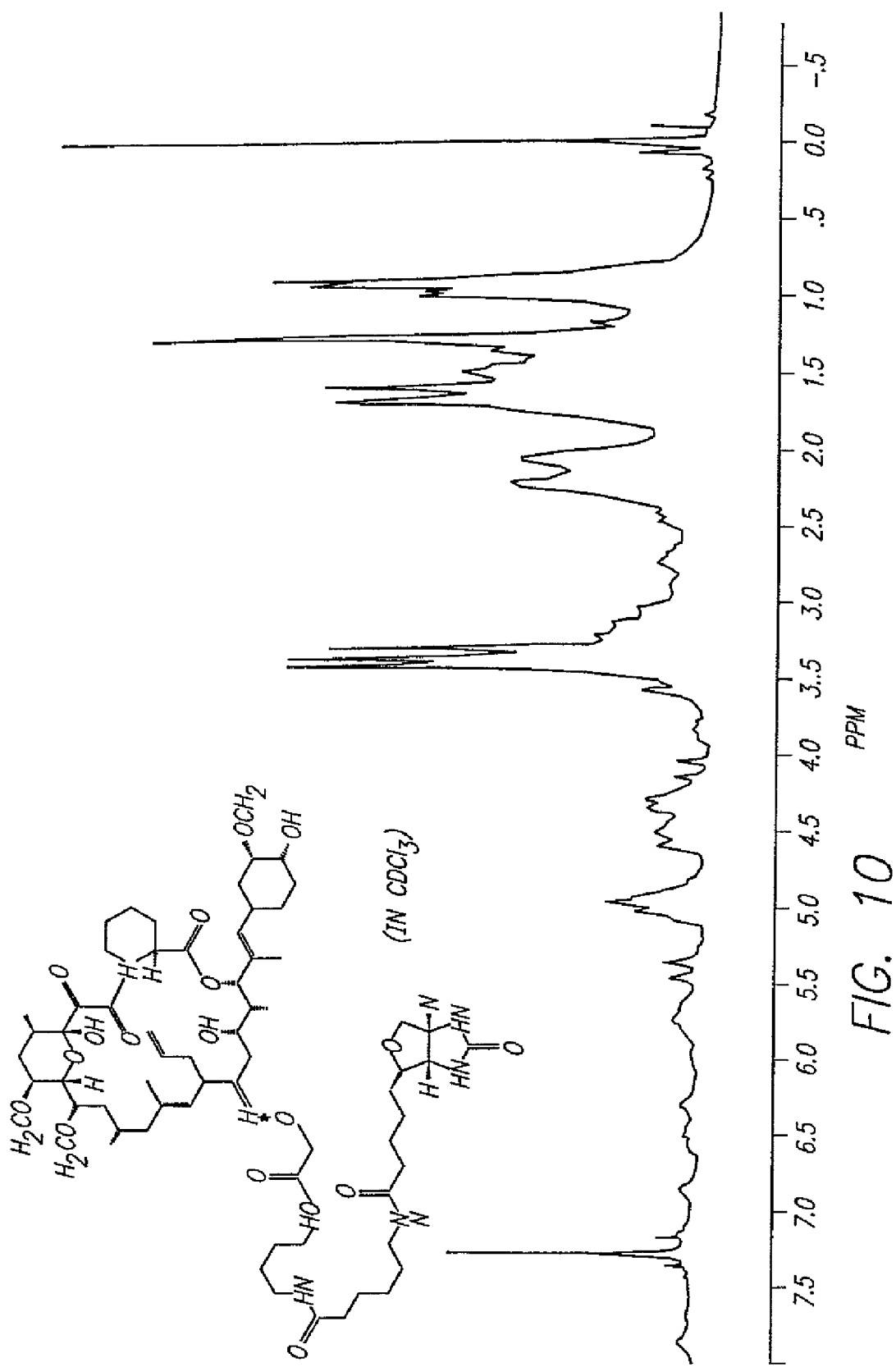
FIG. 10 is a $^1$H NMR spectrogram at 250 MHz in CDCl$_3$ of the product resulting from the reaction of LC-biotin with tacrolimus monooxime.

To a solution of tacrolimus monooxime (12 mg, 13.7 µmol) in 0.3 mL of anhydrous dimethylformamide was added EDAC (4 mg, 20.9 µmol, 1.5 equiv.) and N-hydroxysuccinimide (2.7 mg, 23.4 µmol, 1.7 equiv.). The reaction was stirred at room temperature for 1 h under argon. To this was added triethylamine (10 µL, 75 µmol) and a solution of LC-biotin (10 mg, 25 µmol, 2 equiv.) in 1.0 mL of DMF. Stirring was continued for another 3 h and the mixture was concentration under high vacuum to give a colorless residue. Reversed phase preparative thin-layer chromatography (PTLC) of the crude product on a C-18 plate from Whatman ($PKLC_{18}F$, 20×20 cm, 1000 microns) (13:7 MeOH/$H_2O$) afforded 8 mg of the product as a white solid. The expected result from LSIMS of $C_{64}H_{103}N_7O_{16}S$ is $[M+H]^+$ of 1258.5. The mass spectroscopy results are shown in FIGS. 8 and 9. FIG. 9 represents a section of the spectrum of FIG. 8 at higher resolution centered around the region of interest. $^1$H NMR at 350 MHz in $CDCl_3$ was performed; the results are shown in FIG. 10.

This is an example of derivatization of tacrolimus at position 22.

Example 4

Preparation of Bromoacetyl Derivative of Tacrolimus

Another derivative of tacrolimus derivatized at position 22 is a bromoacetyl derivative. The bromoacetyl derivative can react a sulfhydryl residue of an enzyme or another protein to produce a tacrolimus-enzyme conjugate.

To form the bromoacetyl derivative of tacrolimus, first, to a solution of succinimidyl bromoacetate (740 mg, 3.14 mmol) in 6 ml of tetrahydrofuran (THF) at 4° C. under argon was added, dropwise via a syringe, neat mono-N—BOC-ethylenediamine. After the addition was complete, the reaction was warmed to room temperature and stirred for 3 h. The reaction solution was then concentrated in vacuo, and the residue dissolved in ethyl acetate. The ethyl acetate layer was washed with $H_2O$ once, saturated aqueous $NaHCO_3$ twice, and brine once, dried over $MgSO_4$, and evaporated to dryness to give 440 mg of crude white solid. Purification on silica gel using Chromatotron (1:19 MeOH/$CH_2Cl_2$) afforded 386 mg of pure bromoacetyl ethylenediamine-mono-t-BOC as a white solid.

To a solution of bromoacetyl ethylenediamine-mono-t-BOC (50 mg, 0.178 mmol) in 2 ml of $CH_2Cl_2$ at room temperature was added dropwise via a syringe neat trifluoroacetic acid (TFA) (0.29 ml, 3.76 mmol). The reaction was stirred for 3 h and then concentrated under vacuum. Trace amounts of TFA were azeotropically removed with toluene, and the resulting yellow oily product, the TFA salt of bromoacetyl ethylenediamine, was used directly in the next reaction.

To a solution of the carboxymethyloxime derivative of tacrolimus (derivatized at position 22) (100 mg, 0.14 mmol) and N-hydroxysuccinimide NHS) (19 mg, 0.165 mmol) in 2 ml of THF under argon was added via a syringe neat diisopropyl carbodiimde (DIC) (23 µl, 0.147 mmol). The reaction was stirred at room temperature for 3 h and was then transferred via a syringe to a solution of the TFA salt of bromoacetyl ethylenediamine (0.178 mmol) in 3 ml of THF. To this reaction solution was then added neat diisopropylethylamine (DIEA) (40 µl), 0.23=mol). Stirring was continued for 2.5 h, and the reaction was concentrated in vacuo to give a crude oil. Purification on preparative thin-layer chromatography (TLC) (7:3:1 EtOAc/$CH_2Cl_2$/MeOH) afforded 44 mg (37%) of bromoacetyl tacrolimus as a colorless solid.

Example 5

Preparation of Monoclonal Antibody to Tacrolimus

Preparation of Monoclonal Antibody to Tacrolimus was Performed as follows. The immunogen was the tacrolimus conjugate with keyhole limpet hemocyanin of Example 2. This immunogen was used to immunize Balb/c mice. The first immunization was 25 µg in a volume of 200 µl with monophosphoryl lipid A and synthetic trehalose dicorynomycolate adjuvant (RIBI MPL+TDM Emulsion, RIBI ImmunoChem Research Inc.) intraperitoneally. Five weeks later a boost immunization was given with 25 µg of the immunogen in 200 µl of monophosphoryl lipid A and synthetic trehalose dicorynomycolate adjuvant intraperitoneally. Subsequently, after another 8 weeks, a prefusion boost was given of the 25 µg of the immunogen in 200 µl of Hanks' Balanced Salt Solution intravenously and intraperitoneally.

Three days later the fusion was performed by standard methods using a nonsecreting murine myeloma designated P3x63-AG8.653.

Cloning was done by standard methods.

The clones were screened by the following reverse ELISA immunoassay procedure according to the following protocol. Plates were coated with polyclonal goat anti-mouse IgG (IgG+IgA+IgM) (Zymed) at 5 µg/ml in phosphate buffered saline at 100 µl per well. Plate coating was performed for 2 hours or more at room temperature or overnight at about 4° C.; the plates could be stored wrapped in film at about 4° C. for several days. The plates were then flicked dry and blocked with 300 µl per well of blocking buffer diluent (0.5% bovine serum albumin, 0.05% Tween 20 in PBS). Plate blocking was performed by incubation for 15 minutes or more at room temperature with plate shaking. The plates were then flicked dry. The monoclonal antibody to be screened was then added to each well as follows: 50 µl per well of blocking buffer diluent was added along with 50 µl per well culture supernatant transferred from the corresponding well in the fusion growth plate. Incubation was for about 1 hour at room temperature with plates shaking. The plate was washed using a Titerteck Plus plate washer with S20 stacker with the washing buffer being PBS with 0.05% Tween 20. An enzyme conjugate of tacrolimus covalently coupled to glucose-6-phosphate dehydrogenase diluted in blocking buffer diluent to 1:4000 was added at 100 µl per well. Incubation was performed for about 1 hour at room temperature with shaking. The plate was then washed and a chromogenic solution was added at a volume of 100 µl per well. The chromogenic solution contained 0.593 mM p-iodonitrotetrazolium violet, 0.02 M NAD, 0.033 M glucose-6-phosphate, 0.055 M Tris, 0.02% sodium azide, and a 1:4000 dilution of diaphorase (lipoyl dehydrogenase) (Sigma, St. Louis, Mo.). BSA was present at 1% (vol/vol) of a 5% w/vol BSA solution. BSA was used to help prevent rapid precipitation of reduced p-iodonitrotetrazolium violet.

From the screening a hybridoma producing a suitable monoclonal antibody was selected. This is designated as 1H6 and is a $IgG_1\lambda$ antibody. This antibody has a binding affinity for tacrolimus of about $3.7\times10^9$ liters/mole, that cross-reacts with 13-demethyl tacrolimus, and that has less than about 8% cross-reactivity to all of the following tacrolimus metabolites: 15-demethyl tacrolimus; 31-demethyl tacrolimus; 13,31-didemethyl tacrolimus; 15,31-didemethyl tacrolimus; and 12-hydroxy tacrolimus.

Example 6

Comparison of Cross-Reactivity with Tacrolimus Metabolites for Monoclonal Antibody of Example 4 and Other Antibodies The antibody of Example 5, another antibody resulting from the cloning and designated 14H04, and other antibodies, were tested for cross-reactivity of tacrolimus metabolites (13-demethyl tacrolimus, 15-demethyl tacrolimus, 31-demethyl tacrolimus, 13,31-didemethyl tacrolimus, 15,31-didemethyl tacrolimus, and 12-hydroxy tacrolimus). All of these metabolites except 12-hydroxy tacrolimus were tested at various levels in hemolysate containing 10 ng/ml of tacrolimus; 12-hydroxy tacrolimus was tested at 10 ng/ml with no tacrolimus in the sample. Methanolic extracts were used in this testing. The standard curve generated for this testing were verified using MORE immunosuppressive drug controls level 1-4, a standard control for these assays (More Diagnostics, Los Osos, Calif.).

All antibodies showed cross-reactivity to 13-demethyl tacrolimus to varying degrees. Cross-reactivity was calculated by the following formula: (cross-reaction value ng/ml)-solvent control value (ng/ml)×100)/metabolite spiked target (ng/ml)=% cross-reactivity.

The results are shown in Table 1. With the exception of 13-demethyl tacrolimus, the 1H6 antibody of Example 5 had less than 8% cross-reactivity with the other analytes tested.

TABLE 1

| CROSS-REACTIVITY OF ANTIBODIES WITH TACROLIMUS METABOLITES | | | | | | |
|---|---|---|---|---|---|---|
| Metabolite in Hemolysate | Tacrolimus Present | 14H04 | 1H6 | 6D5-D11 | 6D5-D12 | 6D5-F12 |
| 13-demethyl tacrohmus 5.0 ng/mL | 10 ng/mL | 227% | 78% | 120% | 87% | 65% |

TABLE 1-continued

CROSS-REACTIVITY OF ANTIBODIES WITH TACROLIMUS METABOLITES

| Metabolite in Hemolysate | Tacrolimus Present | 14H04 | 1H6 | 6D5-D11 | 6D5-D12 | 6D5-F12 |
|---|---|---|---|---|---|---|
| 15-demethyl tacrolimus 5.0 ng/mL | 10 ng/mL | 8% | 5% | 9% | 4% | 0 |
| 31-demethyl tacrolimus 5.0 ng/mL | 10 ng/mL | 31% | 7% | 13% | 8% | 0 |
| 13,31 di demethyl tacrolimus 5.0 ng/mL | 10 ng/mL | 10% | 0 | 42% | 0 | 0 |
| 15,31 di demethyl tacrolimus 5.0 ng/mL | 10 ng/mL | 0 | 0 | 29% | 14% | 0 |
| 12-OH tacrolimus 10 ng/mL | 0 ng/mL | 0 | 0 | 0 | 0 | 0 |

Example 7

Homogeneous Immunoassay Using Monoclonal Antibody to Tacrolimus

Figure 11:
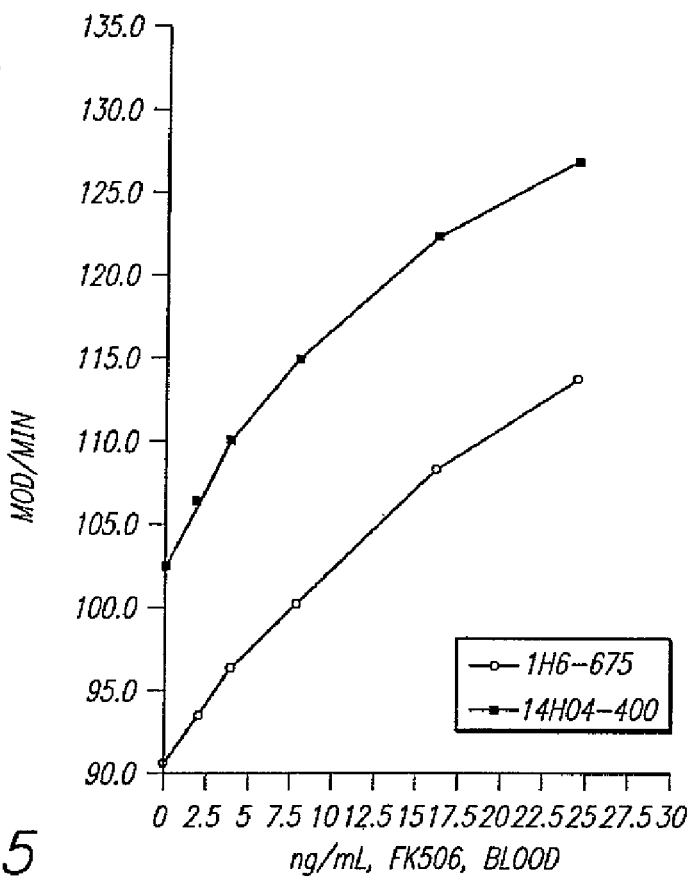
FIG. 11 is a calibration curve of a homogeneous enzyme immunoassay of tacrolimus using a monoclonal antibody produced by immunization of mice with a conjugate of tacrolimus derivatized at position 22 with a carboxymethyl oxime linked to keyhole limpet hemocyanin and cell fusion of the resulting antibody-producing cells with a fusion partner.

A homogeneous immunoassay to tacrolimus based on the EMIT procedure was carried out according to the following protocol. A volume (200 µl) of sample or calibration standard was pipetted into a microfuge tube. Into the same tube, 50 µl of 300 mM $CuSO_4$ was pipetted along with 200 µl of methanol. The mixture was capped and vortexed for 10 seconds and centrifuged for 5 minutes at 20800×g. The supernatant was decanted into a sample cup of a Roche Cobas Mira analyzer according to standard parameters for that analyzer. The following reagents were placed into the reagent rack of the analyzer: Reagent A contained NaCl, $Na_2EDTA$, anti-tacrolimus monoclonal antibody (1H6), nicotinamide adenine dinucleotide (NAD), glucose-6-phosphate, detergent (Pluronic 25R2), sodium azide, and n-methylisothiazolone at pH 5.5. Reagent B was Tris, pH 8.2, with $Na_2EDTA$, detergent (Pluronic 25R), sodium azide, and n-methylisothiazolone. Reagent C was a tacrolimus-glucose-6-phosphate dehydrogenase conjugate at pH 7.0, in $Na_2HPO_4$, $Na_2EDTA$, bovine serum albumin, detergent (Pluronic 25R2), and sodium azide. The sample and reagent racks are loaded onto the analyzer and the run is started according to the parameters that have been preset. The enzyme rates are printed out during the run in terms of milli-od/min. The calibration curves are shown in FIG. 11 for 1H6 and another monoclonal antibody designated as 14H04.

Example 8

Correlation Between Assay for Tacrolimus Using Monoclonal Antibody of the Present Invention and EMIT Assay with LC-MS/MS Method A series of samples from 70 patients to whom tacrolimus had been administered was assayed with the EMIT-homogeneous immunoassay using the 1H6 monoclonal antibody of the present invention as compared with the LC/MS/MS method. The LC/MS/MS method is an assay method for tacrolimus that employs liquid chromatography followed by tandem mass spectroscopy (P. J. Taylor et al., "Sensitive, Specific Quantitative Analysis of Tacrolimus (FK506) in Blood by Liquid Chromatography-Electrospray Tandem Mass Spectrometry," *Clin. Chem.* 42: 279-285 (1996)). The results are shown in FIG. 12. The results show a very high correlation with a correlation coefficient of 0.929.

Example 9

Comparison of Results Using EMIT Homogeneous Immunoassay and LC/MS/MS Using Specimens from Patients with Liver Dysfunction Although monoclonal antibody 1H6 has substantially minimized cross-reactivity to metabolites of tacrolimus other than 13-demethyl tacrolimus, some cross-reactivity remains with 13-demethyl tacrolimus. In order to determine whether or not the cross-reactivity with 13-demethyl tacrolimus would interfere with use of this antibody in an immunoassay, a panel of specimens from 70 patients who had severe liver dysfunction and were awaiting transplantation while on tacrolimus was assayed with the EMIT immunoassay using the 1H6 monoclonal antibody, with the LCMS/MS method, and with another commercially available immunoassay for tacrolimus, the IMx immunoassay produced by Abbott. Such samples typically contain higher levels of tacrolimus metabolites than do those from patients who have undergone organ transplantation but have normal liver function. Tacrolimus levels were measured on the panel of samples using these three assays.

Figure 15:
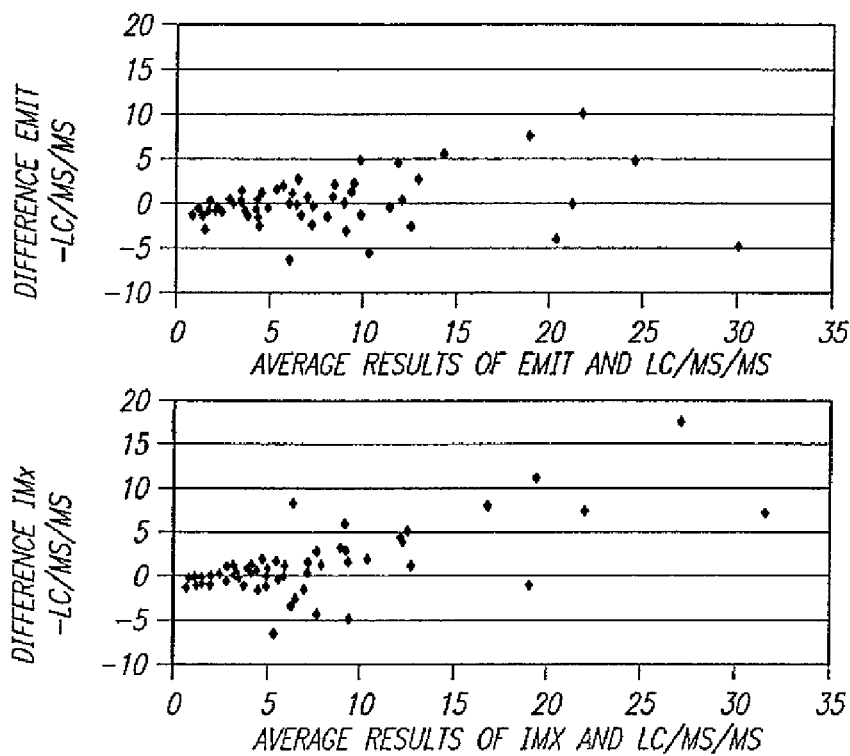
FIG. 15 is a graph showing a Bland-Altman difference analysis plot for the results of FIGS. 13-14.
Figure 16:
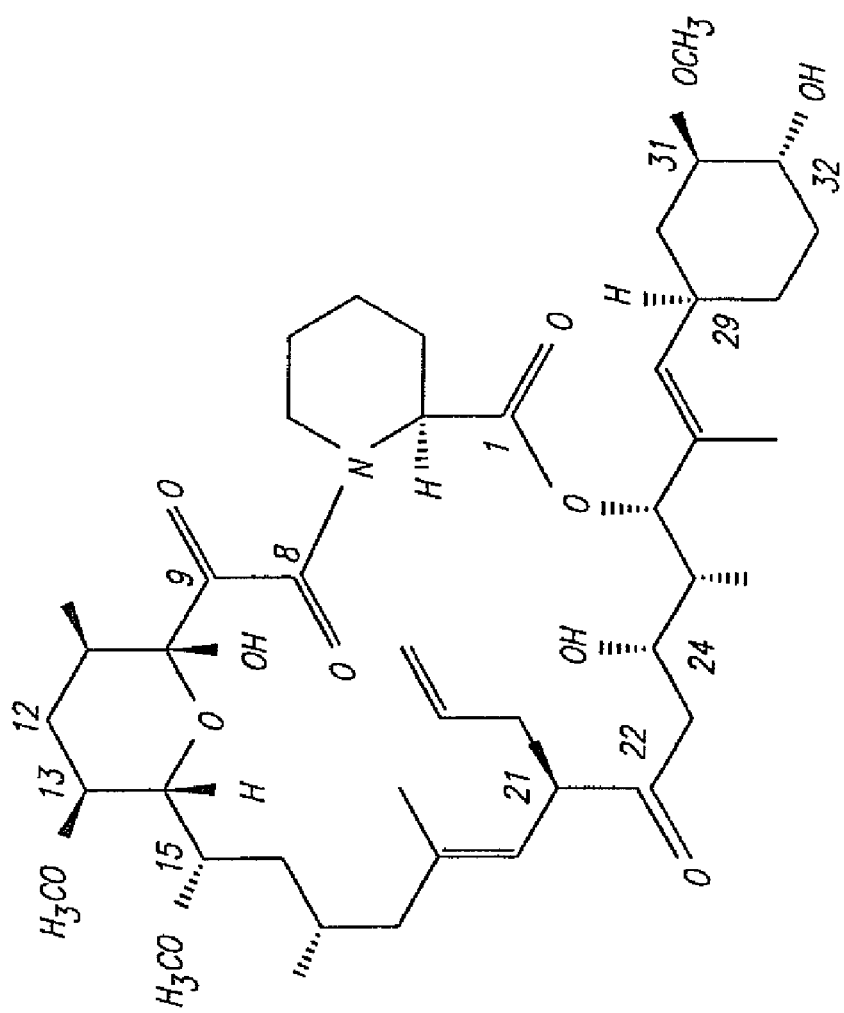
FIG. 16 is a drawing of the structural formula for tacrolimus, showing the numbering of the molecule.

The results are shown in FIG. 13 for the comparison between the EMIT assay and the LC/MS/MS assay and in FIG. 14 for the comparison between the EMIT assay and the IMx assay (Abbott). Deming's regression analysis was used to interpret the results; the results are shown in Table 2. The EMIT assay using the 1H6 monoclonal antibody had closer agreement with LC/MS/MS than the Abbott IMx assay based on the slope of the results (see Table 2) with the slope of 1.11 for EMIT and 1.45 for IMx. Average concentration of the 70 samples of 6.79 ng/ml by MC/MS/MS, 6.96 ng by EMIT using the 1H6 monoclonal antibody, and 7.93 ng/ml by Abbott IMx. Two samples tested above range by IMx only. Bland-Altman analysis of the 70 results are shown in FIG. 15 for EMIT using monoclonal antibody 1H6 and Abbott IMx versus LC/MS/MS. These plots illustrate that in general noticeable variability of results versus LC/MS/MS occurs with samples about 10 ng/ml. The pattern of difference for LC/MS/MS by immunoassay was similar for the EMIT assay using monoclonal antibody 1H6 and the Abbott IMx assay.

TABLE 2

Correlation Between Results of Assays for Tacrolimus in Patients with Liver Damage

| Comparison | Slope/Intercept | Correlation |
|---|---|---|
| EMIT vs. LC/MS/MS | y = 1.11x − 0.66 | 0.910 |
| IMx vs. LC/MS/MS | y = 1.47x − 2.11 | 0.925 |
| EMIT vs. IMx | y = 0.77x + 0.87 | 0.953 |

Even in these patients containing high levels of tacrolimus metabolites, the assay using the monoclonal antibody 1H6 in an EMIT homogeneous immunoassay showed a high degree of correlation relative to other methods. Therefore, liver dysfunction may not cause a severe impact on this assay using this antibody and the results imply that clinical management of patients by immunoassay can be accomplished similarly by using the EMIT immunoassay with the 1H6 monoclonal antibody or the previously-available Abbott IMx immunoassay for tacrolimus. This shows the clinical capability of the 1H6 monoclonal antibody.

ADVANTAGES OF THE PRESENT INVENTION

The present invention provides a monoclonal antibody to tacrolimus that minimizes cross-reactivity with tacrolimus metabolites. The monoclonal antibody of the present invention can be used in an improved immunoassay for tacrolimus that correlates well with other immunoassay methods and non-immunological assay methods for tacrolimus. An immunoassay employing a monoclonal antibody is suitable for clinical monitoring of patients receiving tacrolimus, including patients with impaired liver function who are expected to have high levels of tacrolimus metabolites in their serum.

Although the present invention has been described with considerable detail, with reference to certain preferred versions thereof, other versions are possible. Therefore, the spirit and scope of the appended claims should not be limited to the description of the preferred versions contained herein.

We claim:

1. A monoclonal antibody to tacrolimus produced by fusion of antibody-producing cells from an antibody-producing mammal immunized with tacrolimus derivatized with a carboxymethyl oxime moiety at carbon atom 22 of tacrolimus conjugated to a high molecular weight protein with a suitable fusion partner.

2. The monoclonal antibody of claim 1, wherein the high molecular weight protein is keyhole limpet hemocyanin.

3. An antibody to tacrolimus produced by immunization of an antibody-producing mammal with tacrolimus derivatized with a carboxymethyl oxime moiety at carbon atom 22 of tacrolimus conjugated to a high molecular weight protein.

4. The antibody of claim 3, wherein the high molecular weight protein is keyhole limpet hemocyanin.

5. A conjugate comprising the antibody of claim 1 conjugated directly or indirectly to a detectable label.

6. The conjugate of claim 5 wherein the detectable label is selected from the group consisting of an enzyme label, a radioactive label, a fluorescent label, a chemiluminescent label, a bioluminescent label, and a particulate label.

7. The conjugate of claim 6 wherein the label is an enzyme label.

8. A conjugate comprising the antibody of claim 3 conjugated directly or indirectly to a detectable label.

9. The conjugate of claim 8 wherein the detectable label is selected from the group consisting of an enzyme label, a radioactive label, a fluorescent label, a chemiluminescent, a bioluminescent label, and a particulate label.

10. The conjugate of claim 9 wherein the label is an enzyme label.

11. A method of detecting or determining tacrolimus comprising the steps of:
    (a) providing a sample suspected of containing tacrolimus;
    (b) reacting the sample with:
        (i) the antibody of claim 1; and
        (ii) optionally, a tacrolimus analogue; wherein one of the antibody or the tacrolimus analogue is labeled with a label producing a detectable signal; and
    (c) observing or measuring one of:
        (i) the signal associated with tacrolimus bound to antibody;
        (ii) the signal associated with tacrolimus unbound to antibody; or
        (iii) the total signal present;
in order to detect or determine the presence or concentration of tacrolimus in the sample.

12. The method of claim 11 wherein the sample is reacted with a tacrolimus analogue labeled with an enzyme label and the total signal present is observed or measured to detect or determine the presence or concentration of tacrolimus in the sample.

13. A method of detecting or determining tacrolimus comprising the steps of:
    (a) providing a sample suspected of containing tacrolimus;
    (b) reacting the sample with:
        (i) the antibody of claim 3; and
        (ii) optionally, a tacrolimus analogue; wherein one of the antibody or the tacrolimus analogue is labeled with a label producing a detectable signal; and
    (c) observing or measuring one of:
        (i) the signal associated with tacrolimus bound to antibody;
        (ii) the signal associated with tacrolimus unbound to antibody; or
        (iii) the total signal present;
in order to detect or determine the presence or concentration of tacrolimus in the sample.

14. The method of claim 13 wherein the sample is reacted with a tacrolimus analogue labeled with an enzyme label and the total signal present is observed or measured to detect or determine the presence or concentration of tacrolimus in the sample.

15. A test kit comprising, packaged in separate containers:
    (a) the antibody of claim 1; and
    (b) a tacrolimus analogue labeled directly or indirectly with an enzyme label.

16. A test kit comprising, packaged in separate containers:
    (a) the antibody of claim 3; and
    (b) a tacrolimus analogue labeled directly or indirectly with an enzyme label.

* * * * *